United States Patent [19]

Bilstad et al.

[11] Patent Number: 4,458,539

[45] Date of Patent: Jul. 10, 1984

[54] BLOOD FRACTIONATION APPARATUS HAVING COLLECTED VOLUME DISPLAY SYSTEM

[75] Inventors: Arnold C. Bilstad, Deerfield; John T. Foley, Wheeling, both of Ill.

[73] Assignee: Baxter Travenol Laboratories, Inc., Deerfield, Ill.

[21] Appl. No.: 330,899

[22] Filed: Dec. 15, 1981

[51] Int. Cl.$^3$ ............................................... G01F 1/76
[52] U.S. Cl. ....................................... 73/861; 73/296; 177/DIG. 3; 177/211; 604/6; 604/27
[58] Field of Search .......................... 73/223, 296, 861; 128/760, 771; 177/1, 50, 210 FP, 211, 245, DIG. 3; 604/4, 5, 6, 27, 31, 50, 65–67; 364/510, 567; 377/22

[56] References Cited

U.S. PATENT DOCUMENTS

| | | |
|---|---|---|
| 3,375,357 | 3/1968 | Dekker et al. . |
| 3,439,524 | 4/1969 | Rogers . |
| 3,459,182 | 8/1969 | Naftulin . |
| 3,557,789 | 1/1971 | Poitras . |
| 3,655,123 | 4/1972 | Judson et al. . |
| 3,665,169 | 5/1972 | Henderson et al. . |
| 3,674,097 | 7/1972 | Gile . |
| 3,684,875 | 8/1972 | Smith et al. . |
| 3,701,106 | 10/1972 | Loshbough . |
| 3,789,937 | 2/1974 | Strobel et al. . |
| 3,812,923 | 5/1974 | Rock . |
| 3,853,267 | 12/1974 | Cadwell . |
| 3,855,458 | 12/1974 | Motter et al. . |
| 3,860,802 | 1/1975 | Knothe et al. . |
| 3,916,173 | 10/1975 | Williams, Jr. et al. . |
| 3,960,224 | 1/1976 | Silvers . |
| 3,980,871 | 9/1976 | Lindstrom ............................. 377/22 |
| 4,008,405 | 1/1977 | Neumann et al. . |
| 4,013,194 | 3/1977 | Moscarini . |
| 4,041,289 | 8/1977 | Brosh et al. . |
| 4,044,846 | 8/1977 | Matilainen . |
| 4,117,898 | 10/1978 | Moriyama . |
| 4,139,069 | 2/1979 | Domis et al. . |
| 4,144,943 | 3/1979 | Gallo .................................. 177/210 |
| 4,151,844 | 5/1979 | Cullis et al. . |
| 4,267,837 | 5/1981 | Purdy et al. . |
| 4,294,320 | 10/1981 | Bilstad et al. . |
| 4,320,855 | 3/1982 | Ricciardi et al. ..................... 222/56 |
| 4,330,837 | 5/1982 | Itani . |

OTHER PUBLICATIONS

Randall, "A New Uroflowmeter for Routine Clinical Use," Bio-Med Eng., vol. 10, No. 1, pp. 21–24, (1975).

Primary Examiner—Herbert Goldstein
Attorney, Agent, or Firm—Paul C. Flattery; Daniel D. Ryan; Eugene M. Cummings

[57] ABSTRACT

An apparatus for separating and collecting plasma from whole blood includes a volume monitoring system which provides a continuous display of the volume of plasma collected. A transducer circuit within the system develops an electrical signal frequency-dependent on the weight of the collected plasma. The frequency of this signal over a present measurement interval is periodically compared with the frequency of the signal over a preceding measurement interval to develop a difference signal. If the difference is determined to be positive and less than a predetermined maximum collection rate so as to constitute a valid collection increment, the difference is cumulatively added to previous collection increments in a cumulative display counter to provide a collected volume display, and the frequency of the present measurement interval is taken as a frequency of the preceding measurement interval for the next comparison. If the difference is negative, and therefore not a valid collection increment, then no increment is accumulated. If the difference exceeds the predetermined maximum collection rate, and is therefore not a valid collection increment, then no increment is accumulated and the frequency of the preceding measurement interval is not updated. Since the display counter is advanced only for valid collection increments, it provides a display of collected plasma volume, without regard to tare weight changes and physical disturbances to the collection bag.

46 Claims, 15 Drawing Figures

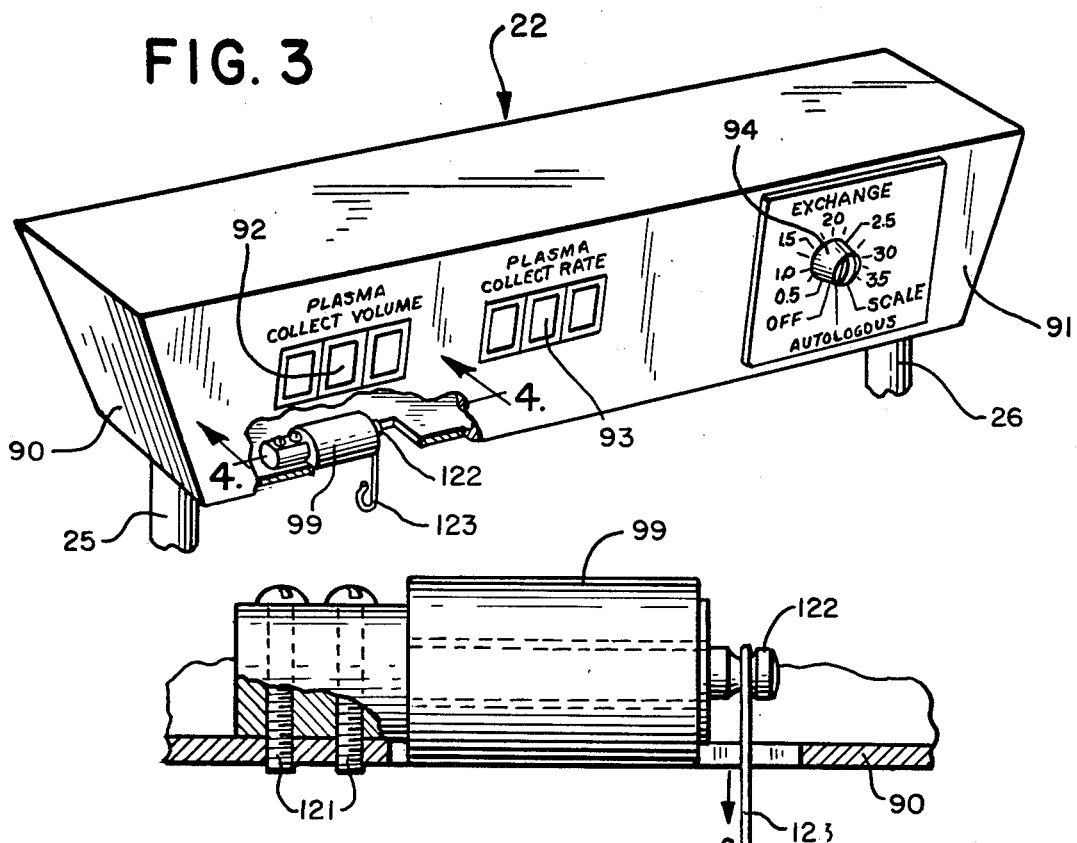

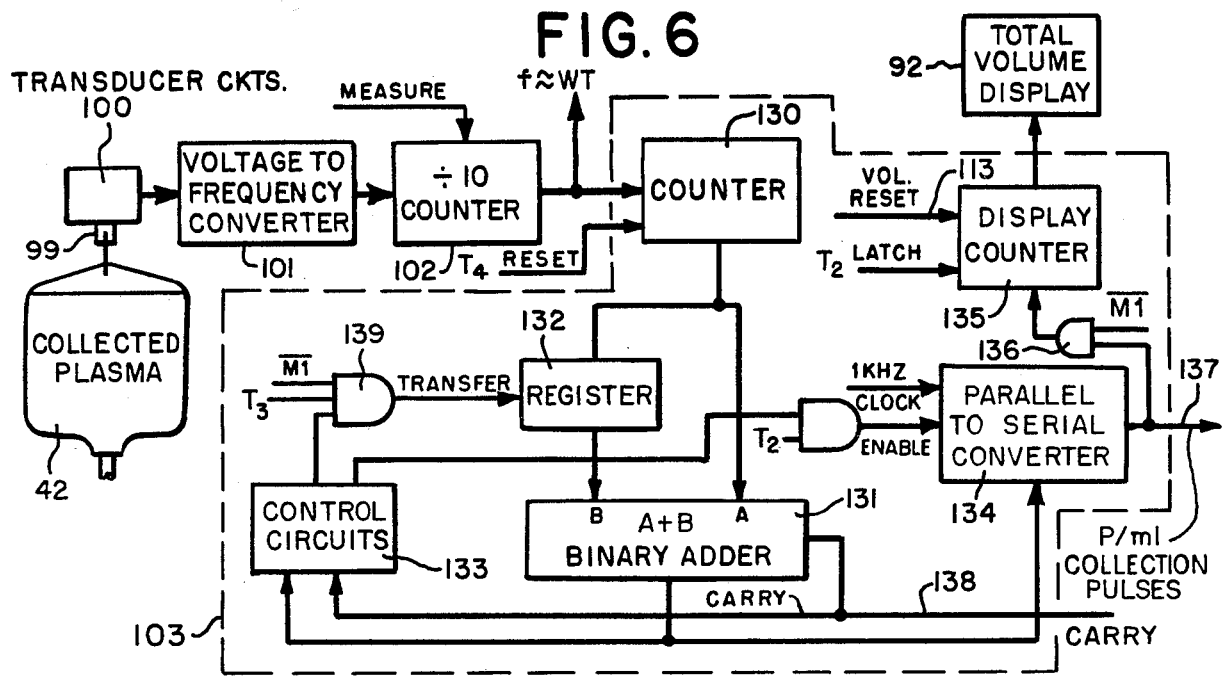
FIG. 6
FIG. 7
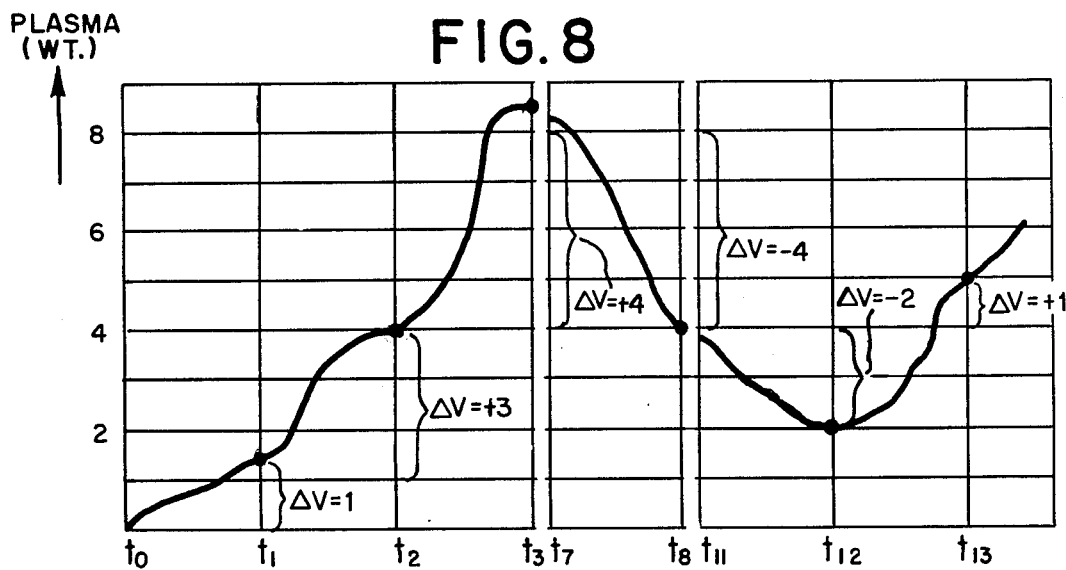
FIG. 8

(RATIO MODE)

(AUTOLOGOUS MODE)

BLOOD FRACTIONATION APPARATUS HAVING COLLECTED VOLUME DISPLAY SYSTEM

BACKGROUND OF THE INVENTION

The present invention relates generally to apparatus for processing whole blood, and more specifically to blood fractionation apparatus for separating and collecting a desired blood component, such as plasma.

Various methods and apparatus have been developed for the continuous flow processing of whole blood, wherein whole blood is taken from a live donor, a desired blood component is separated and collected, a replacement fluid is added to the processed blood, and the processed blood is returned to the donor. Blood components typically collected using such processing include plasma (plasmapheresis), white blood cells (leukopheresis) and platelets (plateletpheresis).

Continuous flow blood processing apparatus may be of the centrifugal type, wherein the differing density of the collected blood component causes the component to congregate for collection at a particular radial distance in a centrifuge, or may be of the filter type, wherein the particle size of the collected component allows only that component to pass through a filter membrane into a collection chamber. Filter type apparatus is generally preferable for continuous flow plasmapheresis applications, since such apparatus does not require complex rotating machinery and is more compact and less costly to manufacture.

One form of filter which is particularly attractive for use in plasmapheresis apparatus utilizes a plurality of parallel microporous hollow fibers arranged side-by-side in the form of a bundle within a hollow cylinder. As whole blood is caused to flow through the fibers the plasma component passes through the walls of the fibers to the surrounding container, which forms a collection chamber from which the component is transported to a collection bag. A preferred construction and method of manufacture of such a hollow fiber filter is shown in the copending application of Robert Lee and William J. Schnell, entitled, "Microporous Hollow Fiber Membrane Assembly and its Method of Manufacture", Ser. No. 278,913, filed June 29, 1981. A preferred form of apparatus for use in conjunction with such a hollow fiber filter is shown in the application of Arnold C. Bilstad and John T. Foley, "Blood Fractionation Apparatus", Ser. No. 330,898, filed concurrently herewith and incorporated herein by reference.

To preclude the collection of too much of one blood component, such as plasma, from a donor, and consequent danger to the donor's health, it is highly desirable that the volume of the blood component collected be monitored and maintained within prescribed limits. Preferably, the volume of the component actually collected and the rate of plasma collection should at all times be displayed in a digital form clearly readable by the operator. Prior art plasmapheresis apparatus relied on the weight of the plasma collection container to provide indications of collected plasma volume and plasma collection rate. One such apparatus is shown and described in the copending application of Arnold C. Bilstad and John T. Foley, entitled, "Apparatus and Method for Weighing Material Being Collected", Ser. No. 140,111, filed Apr. 14, 1980.

One drawback of such prior-art weight-based systems has been the necessity of making mathematical calculations to determine collected volume. Furthermore, it has been necessary to initially obtain the tare weight of the collection container prior to each collection procedure. Moreover, with such systems it has been necessary to reinitiate the collected volume measurement procedure with each change of collection container. This is not only time consuming, but also introduces a potential for error in the volume and rate determinations.

The present invention overcomes these drawbacks by providing a system which automatically determines and displays the volume of a blood fraction collected in plasmapheresis and similar blood fractionation apparatus by analyzing incremental changes in collected plasma weight over successive time intervals. The volume collected is continuously displayed, without consideration of changes in tare weights or changing of the plasma collection container.

It is also desirable in plasmapheresis and other blood fractionation procedures that the rate of collection of the blood component be continuously displayed. This allows the fractionation apparatus to be adjusted for optimum performance, and provides an additional safety check on the operation of the apparatus. In prior art filter-type plasmapheresis systems the collection rate could only be determined by mathematical analysis of collected volumes of plasma over known time intervals. This procedure required an undue amount of time on the part of an operator, and was by its nature often not a sufficiently current indication by which operating adjustments to the apparatus could be made.

The plasmapheresis apparatus described herein incorporates a system wherein plasma collection rate is derived by accumulating and averaging incremental changes in plasma volume, as developed by the previously described volume display system, and is displayed in a clear and unambiguous digital format, allowing the rate display to be used for adjustment of the plasmapheresis apparatus. This system is described in detail in the application of Arnold C. Bilstad and John T. Foley, entitled, "Blood Fractionation Apparatus Having Collection Rate Display System", Ser. No. 330,901, filed concurrently herewith and incorporated herein by reference.

In plasmapheresis procedures it is frequently desirable that a replacement fluid be introduced into the processed plasma-deficient blood to replace the collected plasma prior to returning the processed blood to the donor. In this exchange procedure the replacement fluid is typically introduced by a replacement pump at a fixed volume ratio to the collected plasma, as specified by the attending physician.

In prior art filter-type plasmapheresis systems the speed of the replacement pump, and hence the replacement fluid rate, was manually set by the operator, after observing the plasma collection rate and mathematically calculating the necessary replacement rate from the specified replacement ratio. For each change in collection rate is was necessary to manually reset the replacement rate, and failure to note a change in collection rate resulted in an improper replacement rate.

The plasmapheresis apparatus illustrated herein incorporates a replacement ratio control system which provides an exchange mode wherein the volume of replacement fluid added to the volume of plasma actually collected is automatically proportioned according to an operator-set ratio. The system includes an autologous mode, wherein plasma is withdrawn from the collection container for treatment and return to the donor by the replacement pump at a rate which is automatically set to maintain a constant volume of collected plasma in the collection container. This control system is described in detail in the copending application of Arnold C. Bilstad and John T. Foley, entitled, "Blood Fractionation Apparatus Having Replacement Fluid Ratio Control System", Ser. No. 330,900, filed concurrently herewith and incorporated herein by reference.

SUMMARY OF THE INVENTION

The invention is directed to apparatus for monitoring fluid flow into and out of a container such as the plasma collection container of a plasmapheresis system. The apparatus includes circuit means including an electrical transducer for providing a signal having a frequency related to the weight of the container and the fluid contained therein, and derivation means for deriving from this signal an output signal indicative of incremental units of volume collected in the container.

The invention is further directed to the apparatus as described above, wherein the derivation means includes a counter for providing a cumulative count of units of volume collected, and incrementing means for applying only those output signals to the counter which do not exceed the maximum collection capability of the system to develop an output indicative of total volume collected.

The invention is further directed to the apparatus as described above, wherein the derivation means include means for periodically comparing the frequency of the transducer output signal over a measurement interval with the frequency of the signal over a preceding measurement interval to develop difference signals each indicative of increments of volume collected during the measurement interval.

The invention is further directed to the method for monitoring fluid flow into and out of a container, such as the plasma collection chamber of a plasmapheresis system, wherein a variable frequency signal is provided by a transducer according to the weight of the collection container and the collected fluid, and is compared over successive measurement intervals to develop an output signal indicative of incremental units of volume collected.

The invention is further directed to the method described above, wherein those output signals which do not exceed the maximum collection capability of the system are accumulated in a counter to provide an indication of total volume collected.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 3 is an enlarged perspective view of the overhead collection monitor and replacement rate control unit of the plasmapheresis apparatus of FIG. 1 partially broken away to show the electrical strain transducer incorporated therein.

FIG. 4 is an enlarged side elevational view partially in section of the electrical strain transducer in conjunction with a plasma collection container.

FIG. 5 is a simplified schematic diagram of the circuitry utilized in conjunction with the electrical strain transducer.

FIG. 6 is a simplified block diagram of the collected volume display system of the plasmapheresis apparatus of FIGS. 1 and 2.

FIG. 7 is a logic table useful in understanding the operation of the collected volume display system of the plasmapheresis apparatus.

FIG. 8 is a depiction of certain hypothetical weight variations of the collection container with time useful in explaining the operation of the collected volume display system of FIG. 6.

DESCRIPTION OF THE PREFERRED EMBODIMENT

Figure 1:
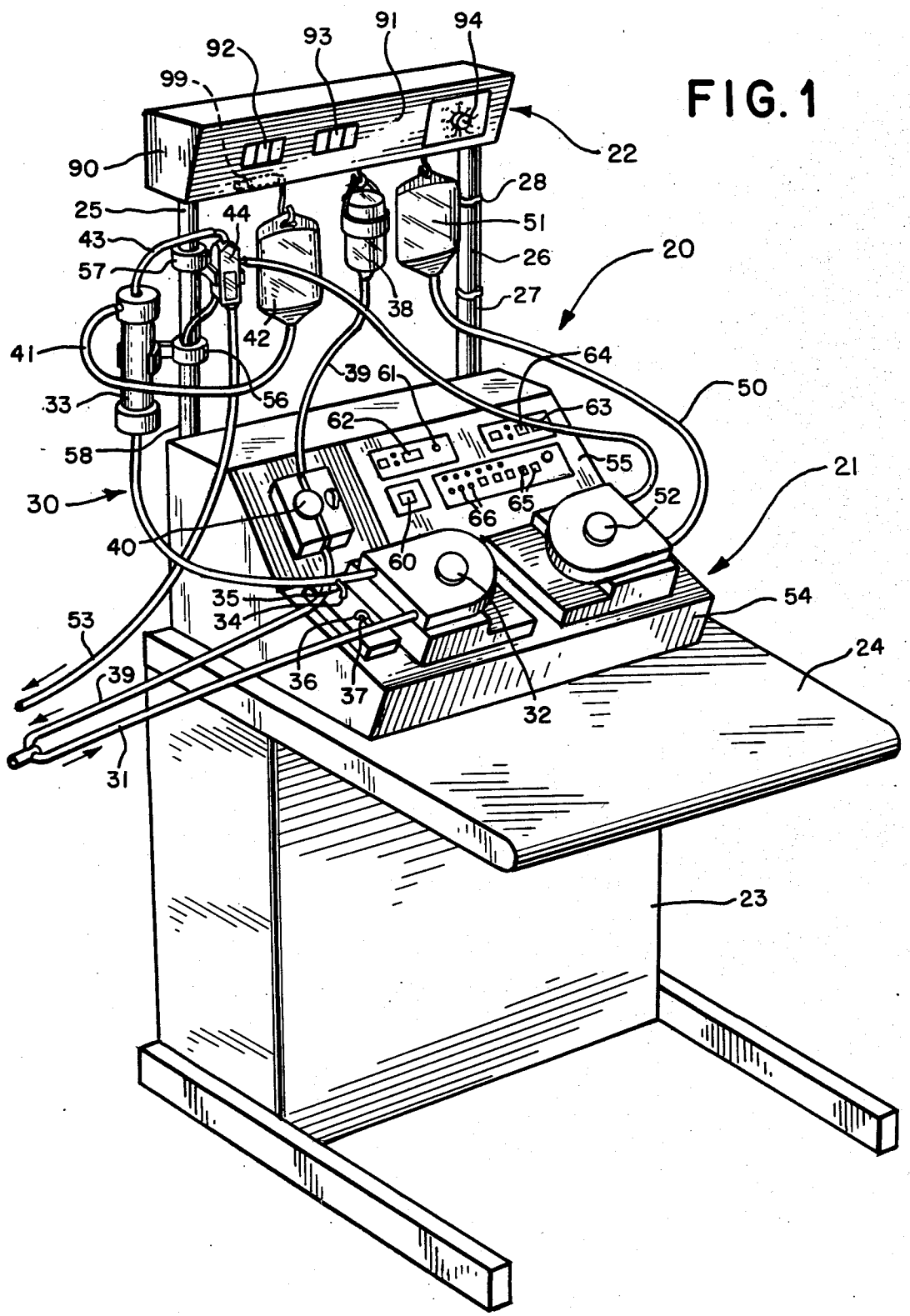
FIG. 1 is a perspective view of plasmapheresis apparatus incorporating a collected volume display system constructed in accordance with the invention.

Referring to the drawings, and particularly to FIG. 1, a plasmapheresis apparatus 20 incorporating the present invention is seen to include a lower table-mounted processing unit 21, and an upper rack-supported collection monitor and reinfusion rate control unit 22. The processing unit is shown mounted on a table 23 of conventional design having a generally horizontal top surface 24 on which the processing unit is supported. However, the processing unit may be removed as necessary from table 23 and installed on other surfaces.

The collection monitor and reinfuse control unit 22 is preferably supported on a pair of vertical support poles 25 and 26 attached to the rear wall (not shown) of the processing unit. As shown in FIG. 1, the separation between the two units is preferably sufficient to allow a plurality of collection and dispensing containers of conventional construction to be hung by appropriate hangers from the bottom surface of the monitoring and control unit. Necessary electrical connections are established between the two units by means of an electrical cable 27 attached to support pole 26 by cable ties 28 or other appropriate fastening means.

Figure 2:
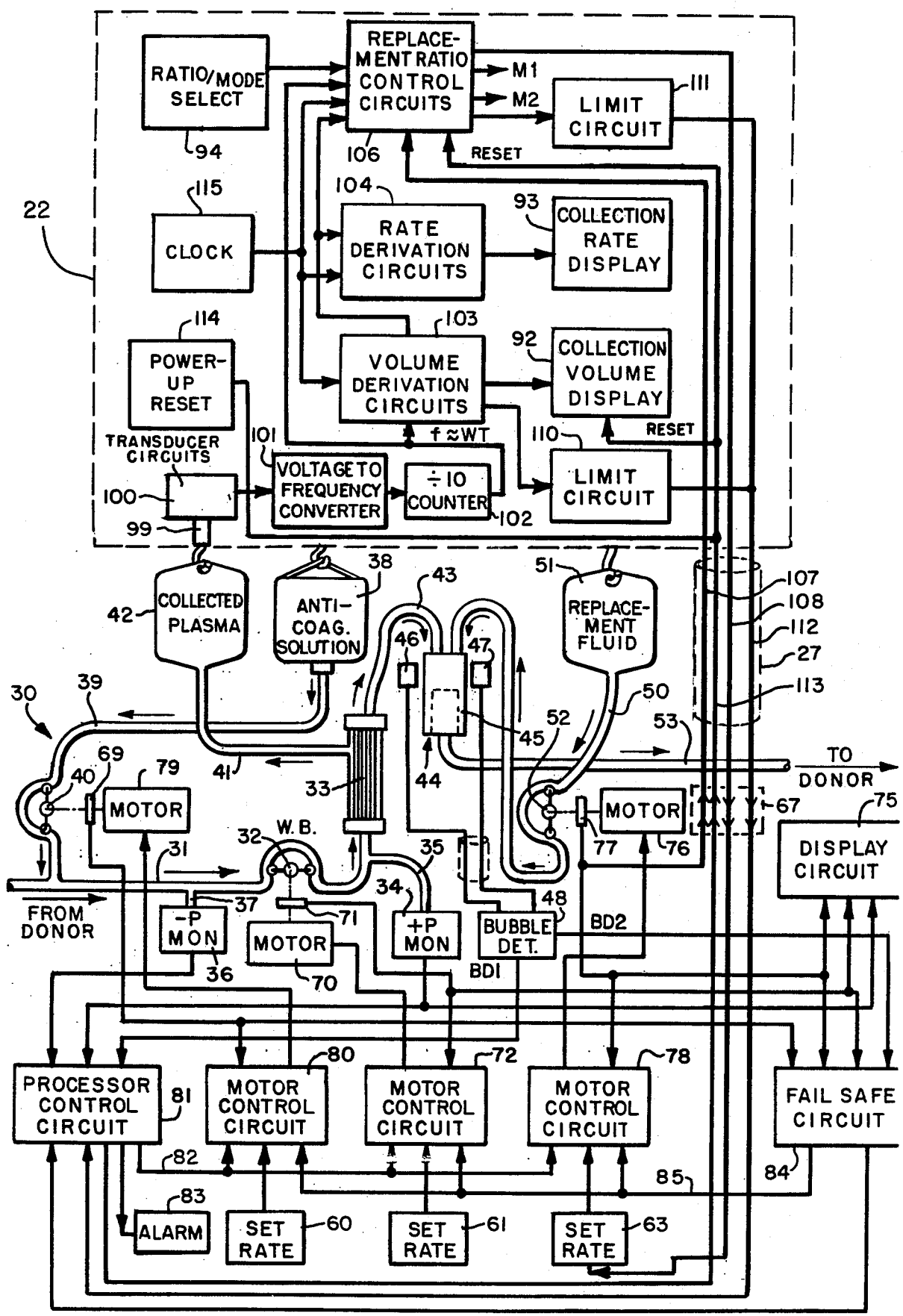
FIG. 2 is a functional block diagram showing the principal components of the plasmapheresis apparatus of FIG. 1.

The processing apparatus 20 is capable of operation in an exchange mode, wherein a desired blood component, such as plasma, is removed from whole blood received from a donor and replaced at an automatically maintained volume ratio by a replacement fluid added to the processed blood prior to the processed blood being returned to the donor; or in an autologous mode, wherein the collected component is automatically removed from the collection container so as to maintain a constant volume in the container, is processed in a secondary treatment system, and is then returned to the donor. A fluid circuit for use in the exchange mode is generally identified by the reference numeral 30 in FIG. 1 and shown schematically in FIG. 2. The fluid circuit 30 includes a plurality of flexible plastic tube segments which form fluid conduits between various components of the fluid circuit. As shown in FIG. 2, whole blood derived from a donor is conveyed through a first tubing segment 31 and a first peristaltic-type whole blood (WB) pump 32 to a hollow fiber-type filter 33 mounted on support rod 25. The operation of the WB pump is monitored by a positive pressure (+P) monitor circuit 34 connected to tubing segment 31 downline of the WB pump by a tubing segment 35. Negative pressure, such as might occur upon the collapse of a vein, is monitored for by means of a negative pressure (−P) monitor circuit 36 connected to tubing segment 31 upline of the WB pump 32 by a tubing segment 37.

To prevent blood from clotting while in process in the apparatus anticoagulant solution from a supply container 38 is introduced at the point of blood withdrawal through a tubing segment 39. A peristaltic-type pump 40 is provided along tubing segment 39 to provide a controlled rate of addition of the anticoagulant fluid to the whole blood.

Plasma separated from the whole blood within the hollow fiber filter 33 is conveyed by a tubing segment 41 to a plasma collection container 42. The pressure provided by WB pump 32 is sufficient to cause flow from the filter to the collection container. The plasma-deficient processed blood from filter 33 is conveyed through a tubing segment 43 to an ultrasonic bubble detector 44, which may be similar in structure and operation to that described in the copending application of Arnold C. Bilstad and Michael Wicnienski, entitled, "Liquid Absence Detector", Ser. No. 127,552, filed Mar. 6, 1980. Basically, bubble detector 44 includes a hollow housing having an internal filter screen assembly 45. Any bubbles in the processed blood fluid collect at the upper portion of the housing. An ultrasonic sound transmitter 46 and an ultrasonic sound receiver 47 positioned at opposite sides of the upper portion of the housing detect bubble formation. The source 46 and detector 47 are connected to a dual bubble detector circuit 48 which provides first and second independent bubble detector (BD) outputs upon the occurrence of a bubble or liquid absence.

Replacement fluid is added to the plasma-deficient blood at this location through a tubing segment 50 which is connected at one end to a replacement fluid container 51 and at its other end to the housing of bubble detector 44. A peristaltic-type replacement pump 52 is positioned along tubing segment 50 to establish a controlled flow rate for the replacement fluid. The combined plasma-deficient whole blood and replacement fluid are pumped from bubble detector 44 back to the donor through a tubing segment 53.

As shown in FIG. 1, the processor unit 21 of plasmapheresis apparatus 20 is housed in a cabinet 54 which includes a sloped front upper portion on which a control panel 55 and the anticoagulant pump 40 are located. The cabinet also includes a sloped front lower portion on which the WB pump 32 and replacement pump 52 are mounted, together with the inlet to the positive pressure monitor 34 and the inlet to the negative pressure monitor 36. When flow system 30 is installed on the plasmapheresis apparatus, the anticoagulant container 38, replacement fluid supply container 51 and plasma collection container 42 are suspended from the overhead monitoring and control unit 22 as shown, and the hollow fiber filter 33 is mounted by means of an appropriate mounting bracket 56 to vertical support rod 25. Bubble detector 44 is similarly mounted to support rod 25 by means of a mounting bracket 57, and the ultrasonic source 46 and detector 47 thereof are electrically connected to processor unit 21 by an electrical cable 58.

Control panel 55 includes operator-actuated controls for operating the plasmapheresis apparatus. These include a selector switch 60 by which the operating speed of the anticoagulant pump 40 is set, a potentiometer control 61 and digital readout 62 by which the operating speed of the WB pump 32 is controlled, and a potentiometer 63 and digital readout 64, by which the operating speed of the replacement pump 52 is controlled. A plurality of pushbutton switches 65 are provided to establish the operating mode of the apparatus, and a plurality of status-indicating lights 66 provide indications of malfunctions in the system.

The processor unit 21 in conjunction with flow circuit 30 constitutes a complete plasmapheresis system which may be operated without monitor and control unit 22. Utilized in this manner, the construction and operation of the apparatus is as described in detail in the previously identified application of Arnold C. Bilstad and John T. Foley entitled, "Blood Fractionation Apparatus", filed concurrently herewith. Thus operated, the system includes no provision for directly indicating the total volume of plasma actually collected or the rate of plasma collection, and no capability for automatically operating the reinfusion pump to maintain a desired volume ratio with plasma collected in the plasma collection container. Instead, during reinfusion the reinfusion rate is calculated from the volume of plasma collected over a known time period, and the result is manually set by means of control 63 and readout 64. The collection monitor and reinfusion control unit of the invention can be easily added at any time by merely plugging cable 27 into a connector 67 (FIG. 2) provided on the processor unit 21.

Basically, within the processor unit 21, the WB pump 32 is driven by a motor 70 having a mechanically coupled tachometer 71. Power for operating motor 70 is provided by a motor control circuit 72 which responds to rate setting means in the form of potentiometer control 61 and a feedback signal from tachometer 71 to maintain a desired motor operating speed. The actual pump flow rate is displayed by readout 62 as part of a display circuit 75, which receives the output signal from tachometer 71.

Similarly, the replacement pump 52 is driven by a motor 76 having an associated tachometer 77. Power for motor 76 is provided by a motor control circuit 78 which responds to a feedback signal from tachometer 77 and the rate selected by the panel-mounted potentiometer 63 to maintain a desired constant motor speed. The actual pump flow rate is displayed by readout 64 as part of the display circuit 75.

The anticoagulant pump 40 is driven by a stepper motor 79 having an associated tachometer 69. Drive signals for motor 79 are developed by a motor control circuit 80 which responds to rate selection switch 60 to maintain a desired constant anticoagulant flow rate.

The operation of the various pump motors is controlled by a processor control circuit 81 which includes mode select pushbuttons 65 on front panel 55. System malfunctions, such as negative pressure at pressure monitor 36, or excessive positive pressure at pressure monitor 34, or the occurrence of a bubble or other fluid absence as signaled at the first output (BD1) of the dual bubble detector circuit 48, result in the application of an appropriate signal to the processor control circuit 81. This circuit responds by producing a control signal on a first motor control line 82 for application to the pump motor control circuits 72, 78 and 80 to interrupt operation of the motors. In addition, an alarm 83 associated with the processor control circuit 81 may be sounded and an appropriate one of indicator lamps 66 may be lit to alert the operator.

The processor unit 21 further includes a failsafe circuit 84 which functions to remove power from the pump motors in the event that processor control circuit 81 fails to respond to a system malfunction. To this end, the outputs of motor tachometers 69, 71 and 77 are applied to the failsafe circuit, together with the second output (BD2) of bubble detector circuit 48. Upon the occurrence of a bubble or fluid absence, as signaled by bubble detector circuit 48, failsafe circuit 84 determines from the simultaneously applied tachometer output signals whether the pump motors have in fact stopped and, if motion is detected after a period of time, provides an additional stop signal which removes motor operating power to motor control circuits 72, 78 and 80 on a second motor control line 85.

As shown in FIG. 1, the collection monitor and replacement fluid ratio control unit 22 of plasmapheresis apparatus 20 includes a housing 90 which extends between the vertical mounting posts 25 and 26 at a height sufficient to allow the various collection and supply containers 38, 42 and 51 to be suspended underneath. The housing includes a downwardly inclined front panel 91 on which a first digital readout 92 is mounted for indicating the volume of plasma collected, and a second digital readout 93 is mounted for indicating the rate of plasma collection. A selector switch 94 allows the user to condition monitor and control unit 22 to provide a desired replacement ratio in the exchange mode, or to select the autologous mode, in which with an appropriate flow system a fixed volume of collected plasma is maintained in collection container 42 as plasma is withdrawn, processed and returned to the donor.

As shown in FIG. 2, collection monitor and control unit 22 includes, in accordance with one aspect of the invention, a strain-gauge transducer 99 from which the plasma collection container 42 is suspended. The transducer is incorporated in a circuit 100 which develops an analog output signal having a voltage level dependent on the weight of collection container 42 and the collected plasma therein. The transducer output signal is applied to a voltage-to-frequency converter 101 which develops in a manner well known to the art a variable frequency weight-indicative output signal. This signal is applied to a divide-by-ten counter 102. The counter output is applied to volume derivation circuits 103, wherein frequency variations over successive time intervals are analyzed and stored in accordance with the invention to develop a cumulative volume collected signal. This signal is applied to volume display 62, which provides a digital display of plasma volume collected.

Volume derivation circuits 103 also produce collection pulses indicative of each incremental amount or unit of plasma collected. These pulses are applied to rate derivation circuits 104 wherein they are accumulated over a time period to obtain an ouput signal indicative of the plasma collection rate. This signal is applied to rate display 64, which provides a digital display of the plasma collection rate.

The volume collection pulses are also applied to replacement ratio control circuits 106. These circuits compare the number of collection pulses, representing the volume of plasma collected, with replacement motor tachometer pulses conveyed from processor unit 21 over a line 107, representing the volume of replacement fluid replaced, and develop an appropriate analog speed control signal for application to the replacement motor control circuits 78 over a line 108. An operator-selected ratio set by switch 94 is automatically maintained by the ratio circuits.

In the event that volume derivation circuits 103 or ratio control circuits 106 detect an over-limit condition in their processing circuits, respective over-limit circuits 110 and 111 provide an over-limit alarm signal on a line 112 for application to control circuit 81 of the processor unit.

Reset of volume display 62 and ratio control circuits 106 when processor 21 is in the prime mode is accomplished by a reset line 113. Reset is also accomplished during initial power-up of the apparatus by a conventional power-up reset circuit 114 connected to reset line 113. Timing pulses required for the various circuits of unit 22 are provided by a clock circuit 115 within the unit. Basically, this clock circuit provides MEASURE and $\overline{\text{MEASURE}}$ clock pulses which establish measurement intervals, during which certain measurement functions are accomplished, and compute intervals, during which certain signal analysis and data transfer functions are accomplished; and a series of clock pulses T, $-T_4$, which sequence the data processing functions during the compute period.

Referring to FIGS. 3 and 4, the electrical strain-gauge transducer 99 is mounted to the bottom of housing 90 by machine screws 121 or other appropriate mounting means. This transducer, which may be conventional in construction and operation, includes at its unsupported end a protruding sense pin 122 from which the plasma collection bag 42 is suspended by means of a clip 123 or other appropriate means.

As shown in FIG. 5, transducer 99 provides a conventional resistance bridge circuit having an output resistance dependent on the force exerted on sense pin 122. A regulated voltage source 124 is connected to the input terminals of the bridge network, and the output terminals of the network are connected to a differential amplifier 125 in accordance with conventional practice. The output of amplifier 125, which constitutes an analog voltage amplitude dependent on the strain exerted on the transducer, is applied to voltage-to-frequency converter 101. This circuit generates an output signal which has a frequency proportional to the applied analog voltage, and hence to the downward force (or weight) exerted on sense pin 122 of the transducer.

In practice, transducer circuit 100 may be designed in accordance with conventional and well known techniques to provide in conjunction with converter 101 an output signal having a 10 hertz variation in output frequency for each milliliter of plasma collected in plasma collection container 42, and various conventional compensating and offset circuits (not shown in FIG. 5) may be incorporated in the circuitry associated with transducer 99 to obtain a more linear and temperature independent output. Typically, for an offset voltage of one volt at the input of differential amplifier 125, a base frequency of 10,000 hertz may be realized at the output of converter 101.

Referring to FIG. 6, the output signal from voltage-to-frequency converter 101 is applied to a conventional frequency divider 127, which divides the 10,000 hertz signal to develop a 1,000 hertz pulse signal having a deviation of 1 hertz per milliliter of plasma collected.

In accordance with the invention, within volume derivation circuits 103 the 1,000 hertz variable-frequency signal is periodically applied during measurement intervals of fixed time duration to an input counter 130, which counts the pulses during each measurement interval to develop an output signal at the end of each measurement interval indicative of the pulse frequency during the interval. In the illustrated plasmapheresis apparatus, the measurement intervals are obtained by application of a $\overline{\text{MEASURE}}$ clock pulse developed by clock 115 to the inhibit input of frequency divider 127, which has the effect of enabling the divider, and hence counter 130, during measure intervals. By selecting a measurement interval of one second, the counter output at the end of the measurement interval is made to equal the frequency of the transducer signal in hertz. However, other measurement intervals may be selected if appropriate.

Following each measurement interval, the counter output is added in an A+B binary adder 131 with a previous inverted output of the counter, as stored in a latch register 132. Consequently, the output of the binary adder is a difference signal representative of the difference between the two counter outputs. If the difference between the counter outputs represents a collection increment which is physically possible by processor unit 21 in the selected measurement interval (in the present embodiment either 0, 1, 2 or 3 collection units within a one second interval), as determined by logic circuitry within control circuits 133, then the output of the binary adder 131 is converted upon the occurrence of a $T_2$ (latch) clock signal to a serial signal consisting of either 0, 1, 2 or 3 collection pulses within a parallel-to-serial converter 134. These collection pulses are applied to a display counter 135 through an AND gate 136, and to an output line 137 for application to utilization means such as rate deviation circuits 104 and rate control circuits 106 of the apparatus. Display counter 135 periodically displays the accumulated count upon receipt of a $T_2$ (latch) clock pulse.

Display counter 135 accumulates the applied pulses for the duration of each plasmapheresis procedure. By adapting the voltage-to-frequency converter 102 to provide a 1 hertz deviation in frequency for the equivalent weight of each milliliter of plasma collected, the accumulated count in counter 135 may be read out directly on the digital volume collected display 62 as milliliters of plasma collected. Display counter 135 is reset only upon completion of the plasmapheresis procedure by a total volume reset pulse on reset line 113. Counter 135 is periodically reset following each measurement interval by a $T_4$ (reset) clock pulse.

If the output of binary adder 131 is greater than 3 units, representing the physical impossibility in the illustrated plasmapheresis system of more than 3 milliliters of plasma being collected in one second, or of more than 180 milliliters being collected in one minute, then the difference is considered invalid by control circuits 133 as having been caused by a physical disturbance to the collection container and no increment is added to display counter 135. Also, when the output of binary adder 131 is negative, as indicated by the absence of an appropriate carry output on its carry line 138, corresponding to a loss of plasma impossible in the system, the differential is considered invalid and no increment is added.

To provide a meaningful reference from which to measure the diferential, register 132 is latched by $T_3$ (load) clock pulses applied through an AND gate 139 to assume the existing reading of counter 130 after the differential output of binary adder 131 has been analyzed and, if valid, incremented to counter 135. This is done in all instances, except if the differential output of binary adder 131 is negative and less than 3 milliliters. In this case register 132 is not latched and therefore retains the previous count of counter 130, and the subsequent deviation is taken from the stored count. This precludes slight flow irregularities such as might result during normal operation of the apparatus from affecting the count.

Additional protection is provided against physical disturbances to the collection container by circuitry in control circuits 133 which causes the differential output of binary adder 131 to be taken as invalid, and register 132 to not be latched for four measurement intervals, following a differential output from binary adder 131 greater than 3. This prevents small transient disturbances to the collection container or flow system, such as might occur for a period of time following a large disturbance to the flow system or apparatus, or following a change of collection containers, from affecting the accuracy of the collected volume display and the collection pulses prodoced by the flow system.

The operation of the volume derivation system is tabulated for a system having a maximum collection rate of 3 milliliters per second as rules I-IV in FIG. 7. If V is taken as plasma volume (based on weight) in a 1 second interval, and $\Delta V$ as the change in volume (based on weight) between successive one second intervals, then it is seen that only those positive volume changes which are either 1, 2, or 3 milliliters in the one second interval, and therefore fall under rule II, are recognized as valid collection increments to be applied to display counter 135. This is illustrated in FIG. 8 by a hypothetical plot of plasma volume (based on weight) over time intervals $t_0$–$t_{13}$. At an initial time $t_0$ the A and B inputs to binary adder 131 are both identical. Consequently, according to rule III of FIG. 7 the differential output A−B is 0, an increment of 0 is produced, and the collected volume count in counter 135 is 0. At time $t_1$, the immediately preceding count is applied to input A, and the next preceding count is applied by register 132 to input B. The resulting A−B differential signal is +1, and in accordance with rule II a 1 milliliter increment is produced for application to display counter 135, resulting in a cumulative count in that counter of 1.

At time $t_2$ the B input of binary adder 131 is a binary one contained in register 132, and the A input is a binary four from counter 130. The +3 differential results in three pulses being incremented to display counter 135, causing the counter to assume a counting state of 4.

Examination of the curve of FIG. 8 at this time will show that in fact four units of plasma have been collected.

At time $t_3$ register 132 has assumed the four count of counter 130 at the end of the previous measurement interval. Input counter 130 now reads 8, making the differential output of adder 131 a +4. In accordance with rule I of FIG. 7, this results in a 0 increment being supplied to display counter 135. Since the deviation exceeded 3, a four period delay is initiated before binary adder 131 can increment counter 135.

After the four period delay under rule I, any transient disturbances will have dissipated, and the system resumes analyzing received data at time $t_7$. From time $t_7$ to time $t_8$, the indicated volume falls to four units, producing a differential of −4. Under rule IV, a zero is incremented to display counter 135 and another four second delay period $t_8$-$t_{11}$ is initiated. At time $t_{12}$, a differential of −2 is realized. Under rule III this results in no incremental output and no change in the cumulative plasma collection count, which remains a 4 units. However, register 132 is caused to retain its four count from time $t_8$ until time $t_{13}$. At time $t_{13}$ however, a +1 increase is recognized by binary adder 131. This causes an increment of one pulse to be applied to display counter 135, and the resulting count in that register to be 5 units of volume. This volume is displayed by the total volume display 62.

By comparing the collected volume of plasma at time $t_0$ with that at time $t_{13}$, it is seen that 5 units of plasma have in fact been collected. Those large positive or negative excursions (in excess of three milliliters in the illustrated apparatus) are considered by the system as not resulting from plasma collection, but from the application of external forces to the transducer, as when changing the plasma collection container, and are accordingly ignored in computing total volume collected. Similarly, since a negative collection rate is physically impossible, small negative excursions of less than 3 milliliters are viewed by the system as chance events which even themselves out with time, and are therefore not accumulated.

Figure 9:
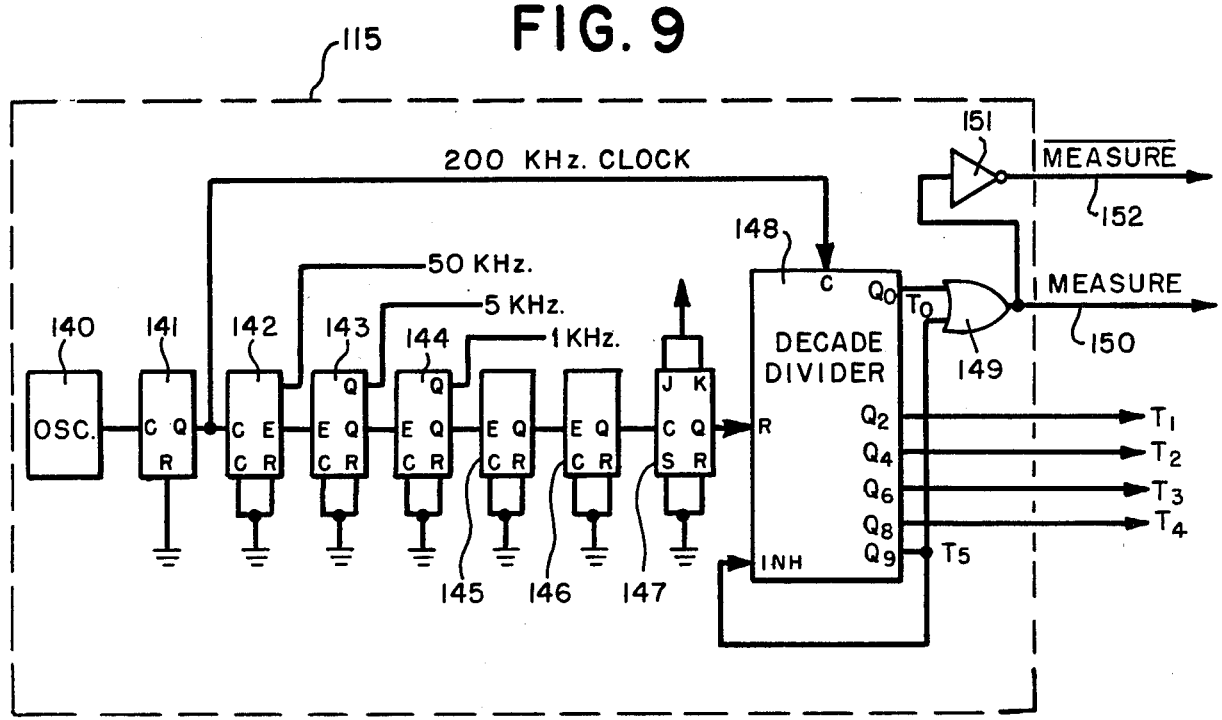
FIG. 9 is a simplified schematic diagram of the clock circuit of the plasmapheresis apparatus of FIGS. 1 and 2.

Referring to FIG. 9, the clock pulses required for operating the various circuits of the collection monitor and reinfuse control unit 22 are supplied by an oscillator 140 six decade counters 141-146, and one flip-flop 147 within clock circuits 115. Counters 141-146 are connected to oscillator 140 in a conventional manner to obtain 200 kHz, 50 kHz, 5 kHz, 1 kHz and 1 Hz clock pulses. The 1 Hz clock pulses and the 200 kHz clock pulses are applied to the reset and clock inputs, respectively, of a decade divider 148. This divider functions as a Johnson counter to produce a series of output pulses $T_1$-$T_4$ following each reset pulse from flip-flop 147. Since the clock pulses applied to the divider are at a relatively high frequency, the sequence of pulses $T_1$-$T_4$ is generated by the divider within a short time interval.

After the divider has completed the pulse sequence $T_1$-$T_4$, an output $T_5$ is generated. This output is applied to the inhibit input of the divider to prevent further counting, and to one input of an OR gate 149. The other input of OR gate 149 receives a $T_0$ output from the divider, causing the gate to produce a MEASURE control signal on a line 150 whenever the divider is reset and not counting. An inverter 151 connected to the output of OR gate 149 produces a NOT-MEASURE control signal on a line 152.

Figure 10:
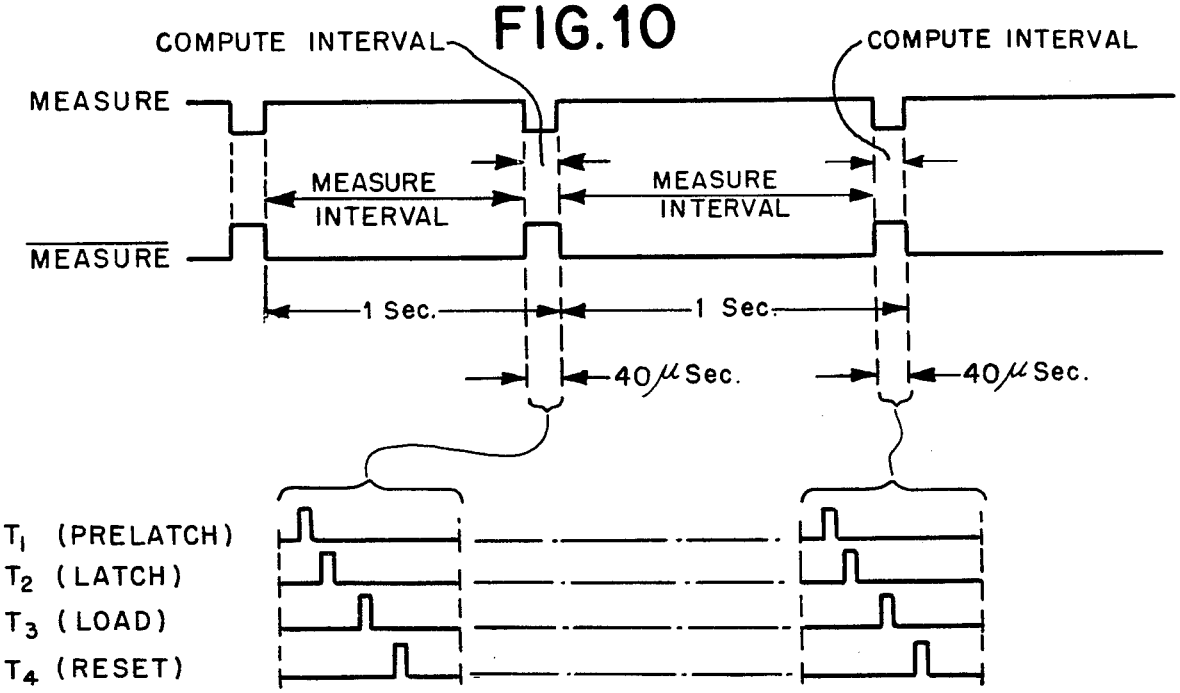
FIG. 10 is a depiction of certain waveforms produced by the clock circuit of FIG. 9 useful in understanding the operation of the collected volume and collection rate display systems of the apparatus.

As illustrated in FIG. 10, the MEASURE control signal developed by decade divider 148 provides the 1 second measurement period during which counter 130 counts pulses from divider 127. Following each such measure interval, upon application of a reset pulse to decade divider 148, a 40 microsecond computing period occurs while divider 148 counts through its cycle. Clock pulses $T_1$-$T_4$, which are associated with prelatch, latch, load and reset functions, respectively, of circuits 103, 104 and 106, occur during this compute period. Since clock pulses $T_1$-$T_4$ are obtained at alternate outputs of divider 148, a time space exists between the clock pulses which precludes any overlap in the functions they control.

Figure 11:
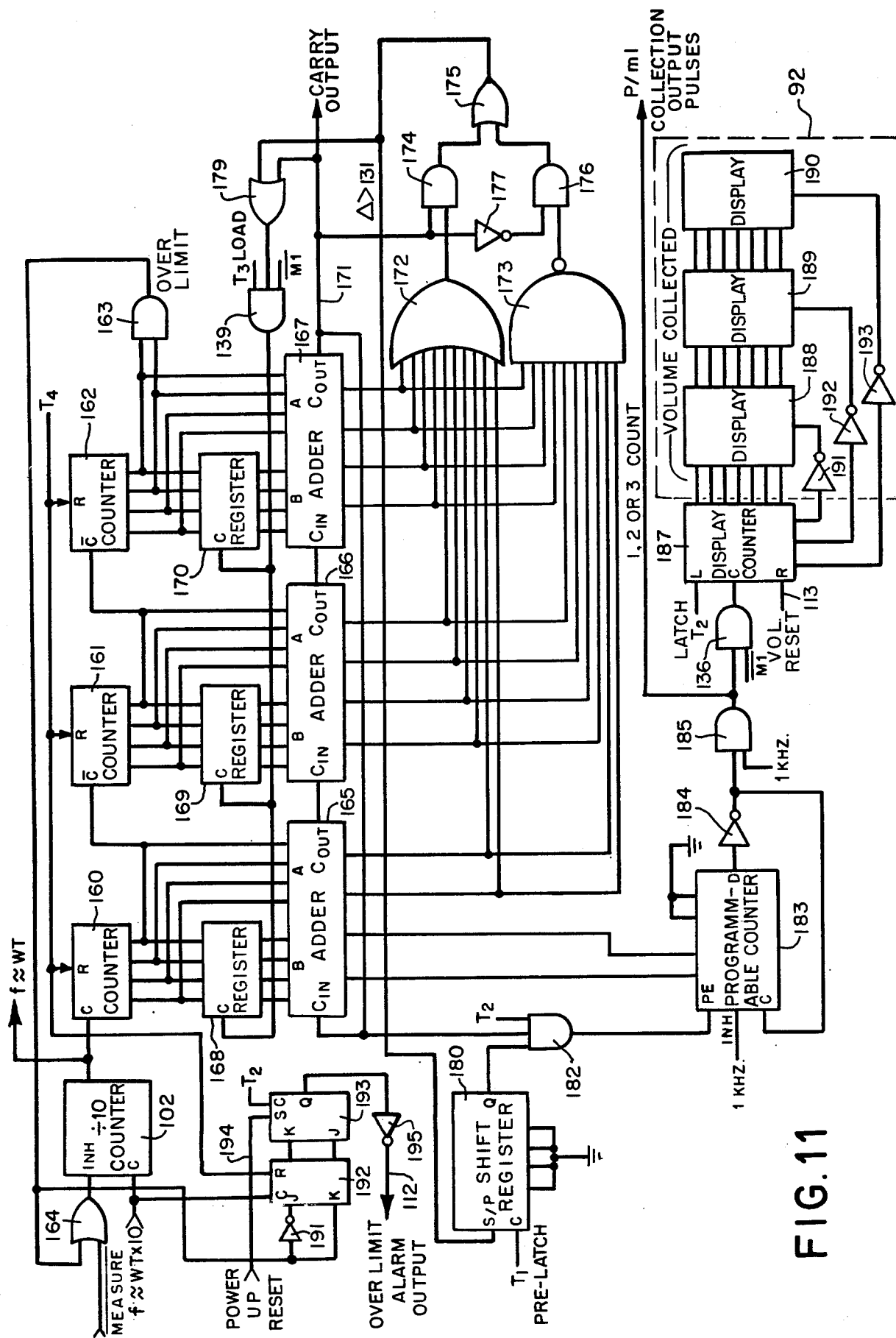
FIG. 11 is a simplified schematic diagram of the collected volume display system of FIG. 6.
Figure 12:
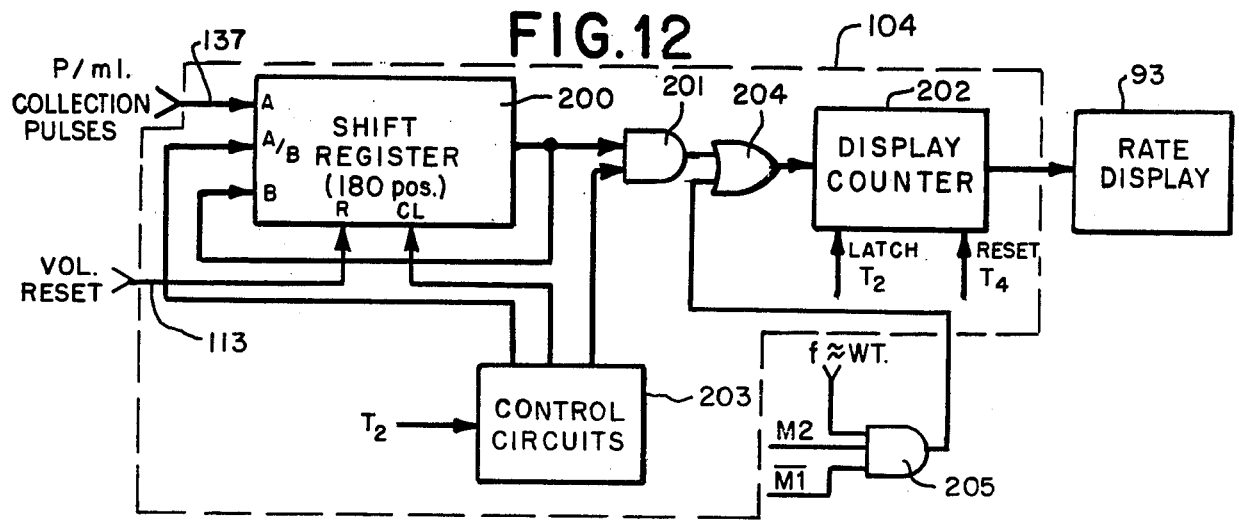
FIG. 12 is a simplified functional block diagram of the collection rate display system of the plasmapheresis system of FIGS. 1 and 2.

Referring to the schematic diagram of the volume derivation circuits shown in FIG. 11, the weight-dependent variable frequency signal from the divide-by-ten counter 127 is applied to a trio of counters 160-162, which collectively perform the function of counter 130 of FIG. 6. The most significant digit of each counter output is taken as the carry output and is connected to the clock input of the next succeeding counter. Thus, the presence of an output signal on the most significant digit of counter 160 results in a carry signal to counter 161, and the presence of a signal on the most significant digit of counter 161 results in a carry signal to counter 162. This allows a total count of 12 digits to be accommodated by the counters.

In the event that a predetermined maximum count allocated to the three counters is exceeded, as evidenced by outputs at the two most significant digits of counter 162, an AND gate 163 produces an over limit indicative output which inhibits counter 127 through an OR gate 164. This over-limit inhibit continues until counters 160-162 are reset following the measurement interval. As previously described, the divide-by-10 counter 127 is inhibited during compute intervals by a MEASURE clock pulse applied through OR gate 164. This prevents the application of transducer pulses to counters 160-162 after a count has been completed, thereby providing an unchanging output from the counters during the comparison period. Counters 160-162 are periodically reset by a $T_4$ clock pulse, which as seen in FIG. 10 occurs at the end of the clock period.

The outputs of counters 160-162, which are in parallel binary format, are applied to the A inputs of respective binary adders 165-167, which collectively perform the function of binary adder 131 in FIG. 6, and to the inputs of respective latch-type registers 168-170, which are each connected to provide an inverted output and which collectively perform the function of latch register 132 in FIG. 6. The outputs of registers 168-170, in binary inverted-parallel format, are applied to the B inputs of respective ones of binary adders 165-167.

To provide the carry function necessary for cooperative operation of the binary adders, the carry output of adder 165 is connected to the carry input of adder 166, and the carry output of adder 166 is connected to the carry input of adder 167. The carry output of adder 167 is connected to the carry input of binary adder 165 by an end-around carry line, and to other circuits within the plasmapheresis apparatus by a carry signal line 138. Adders 165-167, thus connected, function in a manner well known to the art to produce an output signal equal to the difference between the output of counters equal to the difference between the ouput of counters 160-162, applied direct to the A inputs of the adders, and the stored output of the counters, applied through inverted registers 168-170 to the B inputs of the adders.

The parallel binary format outputs of binary adders 165-167 collectively provide a 12-digit signal representing the difference between the binary signals applied to the A and B inputs of the adder devices. The ten most significant digits of this signal are applied to signal analysis means in the form of a 10 input OR gate 172 and a 10 input NAND gate 173. The output of OR gate 172 is applied through an AND gate 174 to one input of an OR gate 175. The output of NAND gate 173 is applied through an AND gate 176 to the remaining input of OR gate 175. The carry output of binary adder 167 is connected to the remaining input of AND gate 174 and through an inverter 177 to the remaining input of AND gate 176.

The arrangement of logic gates 172-177 is such that an output is produced by OR gate 175 only if the output of binary adders 165-167, as determined by the presence or absence of outputs on the ten most significant digits of the twelve digit output signal, exceeds an absolute value of three. In the presence of a carry output from binary adder 167 the difference output is taken as positive, and AND gate 174 is enabled and AND gate 176 is inhibited. In the absence of a carry signal from adder 167 the difference output is taken as negative and AND gate 174 is inhibited and AND gate 176 is enabled. Thus, during a negative output NAND gate 173 is determinative and provides an output only in the presence of a logic low condition on any one of the monitored outputs from the ten most significant digits of adders 165-167. Conversely, during a positive output, gate 172 is determinative and provides an output through OR gate only in the presence of a logic high condition on any one of the monitored outputs of binary adders 165-167.

The output of OR gate 175 is applied to one input of an OR gate 179 and to the parallel enable input of a shift register 180. The other input of OR gate 179 is connected to the carry output of binary adder 167, so that upon the occurrence of a difference in excess of absolute 3, or a positive carry output on line 168, OR gate 179 is enabled. The output of this gate is applied to one input of AND gate 139. Another input of AND gate 139 is connected to receive the $T_3$ (load) clock pulses, and the remaining input is connected to receive an $\overline{M1}$ mode control signal generated in replacement fluid flow ratio control circuits 106 to signal selection by switch 94 of operation of the monitor and control unit 22 in an autologous mode. As a result, registers 168-170 are clocked at time $T_3$ during the compute period to assume the counting state of counters 160-162.

Shift register 180 functions to provide a delay period of four measurement intervals following the occurrence of a differential count in excess of absolute 3. To this end, in the event of a logic low output from OR gate 175, shift register 180 is enabled in a serial mode and provides an output following the application of four $T_1$ (pre-latch) clock pulses to its clock input terminal. This output signal is applied to an AND gate 182 which controls the application of $T_2$ (latch) clock pulses to parallel to serial conversion means in the form of programmable counter 183. These pulses condition counter 183 to a parallel mode.

The two least significant digits of the twelve digit difference signal developed by binary adders 165-167 are applied as a parallel-loaded input to counter 183. In its parallel mode the counter counts either zero, one, two or three pulses, corresponding to the two digit parallel-loaded signal from binary adder 165, before producing an output signal.

The output of counter 183 is applied through an inverter 184 to one input of an AND gate 185, which is also connected to the inhibit input of counter 183 the other input of AND gate 185 is connected to the 1 kHz clock pulse source. Gate 185 is enabled until counter 183 produces an output, so that either zero, one, two or three pulses are produced at a 1 kHz rate at the output of the gate according to the two binary digits applied to counter 183. The output of inverter 184 is also coupled to the clock input of the counter to terminate operation of the counter after the required counting state has been reached.

Counter 183 is prevented from counting when the differential output of adders 165-167 is greater than absolute 3, and for a four interval delay thereafter, or in the event of a negative differential, by AND gate 182, which controls the application of $T_2$ latch pulses to the parallel enable input of the counter. Application of these latch pulses to counter 183 enables the counter to assume the count of the parallel-loaded digits from adder 165.

Counter 183 counts down from the parallel-loaded count, and zero, one, two or three pulses are developed at the output of AND gate 185 and applied through AND gate 136 to a display counter 187. The remaining input of AND gate 136 is connected to the $\overline{M1}$ control line so that gate 136 is inhibited, and the zero, one, two or three pulse increment produced by counter 183 is not applied to the clock input of display counter 187 if the apparatus is in the autologous mode.

Display counter 187 operates in a conventional manner to accumulate the pulses applied by AND gate 136. The accumulated count is transferred to a display output each time a $T_2$ (latch) control signal is applied to the latch input of the counter. The count assumed by display counter 187 is applied to three conventional seven-segment display panels 188-190 which are enabled by counter-generated strobe signals in a conventional manner through inverter amplifiers 191-193 to display the accumulated count with three digit accuracy. The count accumulated in display counter 187 is reset to zero only upon the application of a volume reset signal to the reset terminal of the counter. Normally this occurs on reset line 113 only during initial power-up of the apparatus, or when changing operating modes.

In the event that counters 160-162 exceed a predetermined limit, an alarm is sounded after a one second delay. To this end, the output of AND gate 163 is applied directly and through an inverter 191 to the J and K inputs of a JK type flip-flop 192. $T_4$ (reset) clock pulses are applied to the reset terminal of this flip-flop and the outputs of the flip-flop are coupled to the inputs of a second JK flip-flop 193. The set input of flip-flop 193 is connected to the power-up reset line 194 of the apparatus, so that upon initial power-up flip-flop 193 is not actuated. A limit alarm is provided by the ouput of flip-flop 193 through an inverter 195. The variable-frequency output pulses from voltage-to-frequency converter 102 are applied to the clock input of flip-flop 192 to render the operation of that flip-flop subject to the occurrence of additional output pulses from the transducer circuit.

In operation, the variable frequency signal from voltage-to-frequency converter 102 is applied to counters 160-162, causing these counters to count up until the application of pulses is interrupted by OR gate 164 and counter 127 being inhibited by the $\overline{\text{MEASURE}}$ clock signal at the end of the measurement interval. At this time counters 160-162 provide a 12 digit output signal indicative of the frequency of the applied weight-indicative signal, and adders 165-167 provide an output signal corresponding to the difference between this signal and the previous counter output signal as applied inverted by latch registers 168-170. All but the two least significant digits of the output signal are analyzed by logic gates 172-177 to determine whether the difference is greater than absolute three. If the difference output is less than three, and providing the output is positive as indicated by the presence of a logic high condition at the carry output of binary adder 167, programmable counter 183 is parallel-enabled by a $T_2$ (latch) clock pulse through AND gate 182 and counts down through the number of steps dictated by the applied two least significant digits to produce at the output of AND gate 185 either zero, one, two or three pulses at a 1 kHz rate. These pulses are applied to and accumulated in display counter 187, which upon receipt of the $T_2$ (latch) clock pulse indicates on display panels 188-190 the accumulated volume of plasma collected.

In the event that the carry output of binary adder 167 is logic low, corresponding to a negative output from the binary adders, AND gate 182 is inhibited and counter 183 remains inhibited. This results in no output at AND gate 185 and no incremental pulses being applied to display counter 187. In the event that the difference developed by binary adders 165-167 exceeds an absolute three, shift register 180 is enabled in its parallel mode and inhibits AND gate 182 for four subsequent occurrences of $T_1$ (pre-latch) clock pulses after the difference becomes less than absolute 3. Also, in the event of a negative difference less than three, OR gate 179 inhibits AND gate 139 to prevent registers 168-170 from responding to the next $T_3$ (load) clock pulse to assume the counting state of counters 160-162. As previously explained, this prevents registers 168-170 from assuming a new counting state following a negative incremental change of less than absolute three.

The sequence of the clock pulses $T_1$-$T_4$ is such that the application of pulses to counters 160-162 is first terminated by the measure control signal applied to OR gate 164, after which the delay shift register 180 is stepped by the $T_1$ (pre-latch) clock pulse. Next, AND gate 182 and display counter 187 are enabled by a $T_2$ (latch) clock pulse to transfer data. Then, registers 168-170 are latched to a new count by a $T_3$ (load) clock pulse, after which counters 160-162 are reset by a $T_4$ (reset) clock pulse.

The plasma collection pulses developed by volume derivation circuits 103 are utilized by collection rate derivation circuit 104 to develop a display of plasma collection rate. This circuit, which is described in detail in the copending application of Arnold C. Bilstad and John T. Foley entitled, "Blood Fractionation Apparatus Having Collection Rate Display Systems", filed concurrently herewith, includes a shift register 200 for receiving the plasma collection pulses. This register has data positions for storing the serial data received from volume derivation circuits 103 over sixty preceding one second measurement intervals. Since in the illustrated plasmapheresis apparatus each measurement interval results in the production of either zero, one, two or three milliliter serial collection pulses, or data bits, three data positions are reserved in the register for each of the sixty measurement intervals to be taken into account. Thus, 180 data positions are provided in register 200.

When the three data bits for each measurement interval have been entered into register 200 for the preceding 60 intervals, the register contains a count total equal to the total number of milliliters of plasma collected over the preceding 60 intervals. If each interval is one second in duration, then the counting state of the register represents the number of milliliters collected in the preceding minute, which may be read as the collection rate in milliliters per minute.

The operation of shift register 200 is conventional in that, the addition of each new bit of data at its input results in the overflow of one bit of data at its output. Thus, if three data bits are loaded at its input, three data bits are produced at its output. Since the data bits advance from input to output, the most recent data is located at the input of the register, and the oldest data is located at the output of the register. Consequently, when three data bits are entered representing the most recent data in a 60 second or one minute, analysis period, the three data bits produced at the output represent data occurring before the analysis period. Thus, only collections in the previous minute are recorded in shift register 200.

To provide a display of the rate of plasma collection, the data bits contained in shift register 200 are periodically applied through appropriate switching means such as an AND gate 201 to a display counter 202. To this end, clock pulses are applied to shift register 200 to cause data within the register to appear serially at the output of the register. With AND gate 201 enabled, this data is applied to display counter 202, wherein the total number of collection pulses in the data is accumulated as a count representative of the number of milliliters of plasma having been collected in the preceding analysis period. The total count developed by counter 202 is displayed by collection rate readout 93 in milliliters of plasma collected per minute.

Shift register 200 has A and B inputs selected by application of a signal to its A/B select input. To update the rate display to reflect changes in flow rate, new data consisting of three bits for a new measurement interval is applied to the A input of shift register 200. Control circuits 203 enable the A input and apply appropriately timed clock pulses. The oldest three data bits in the register appear serially at the register output as the new bits are entered. Control circuits 203 inhibit AND gate 201 at this time to prevent the three oldest bits from being applied to display counter 202. Since the B input of the shift register is inoperative (not selected), the bits are not recirculated back into the register and cease to exist.

After the three new data bits have been applied to the A input, control circuits 203 cause the B input to be selected and AND gate 201 to be enabled. Clock pulses now applied to shift register 200 recirculate all 180 data bits in the register from the output back to the B input. At the same time, the same 180 data bits are applied through the enabled AND gate 201 to display counter 202, which has been reset by a $T_4$ (reset) clock pulse prior to the loading operation. After the 180 data bits in the register have completely recirculated, the application of clock pulses to the register is terminated, AND gate 201 is inhibited, and a $T_2$ (latch) clock pulse is applied to display counter 202 to cause that counter to display the count of the pulses just applied. Digital display 93 displays this count to the operator as milliliters of plasma collected per minute.

At the completion of the next measurement cycle a new set of collection data is produced by volume derivation circuits 103. Prior to receiving this data, control circuits 203 condition the A input of shift register 200 operative and inhibit AND gate 201. Then, after the new data has been received, display counter 202 is latched, AND gate 201 is enabled, and an additional 180 clock pulses are applied to shift register 200 to transfer the new data to counter 202 to begin the cycle anew.

Figure 13:
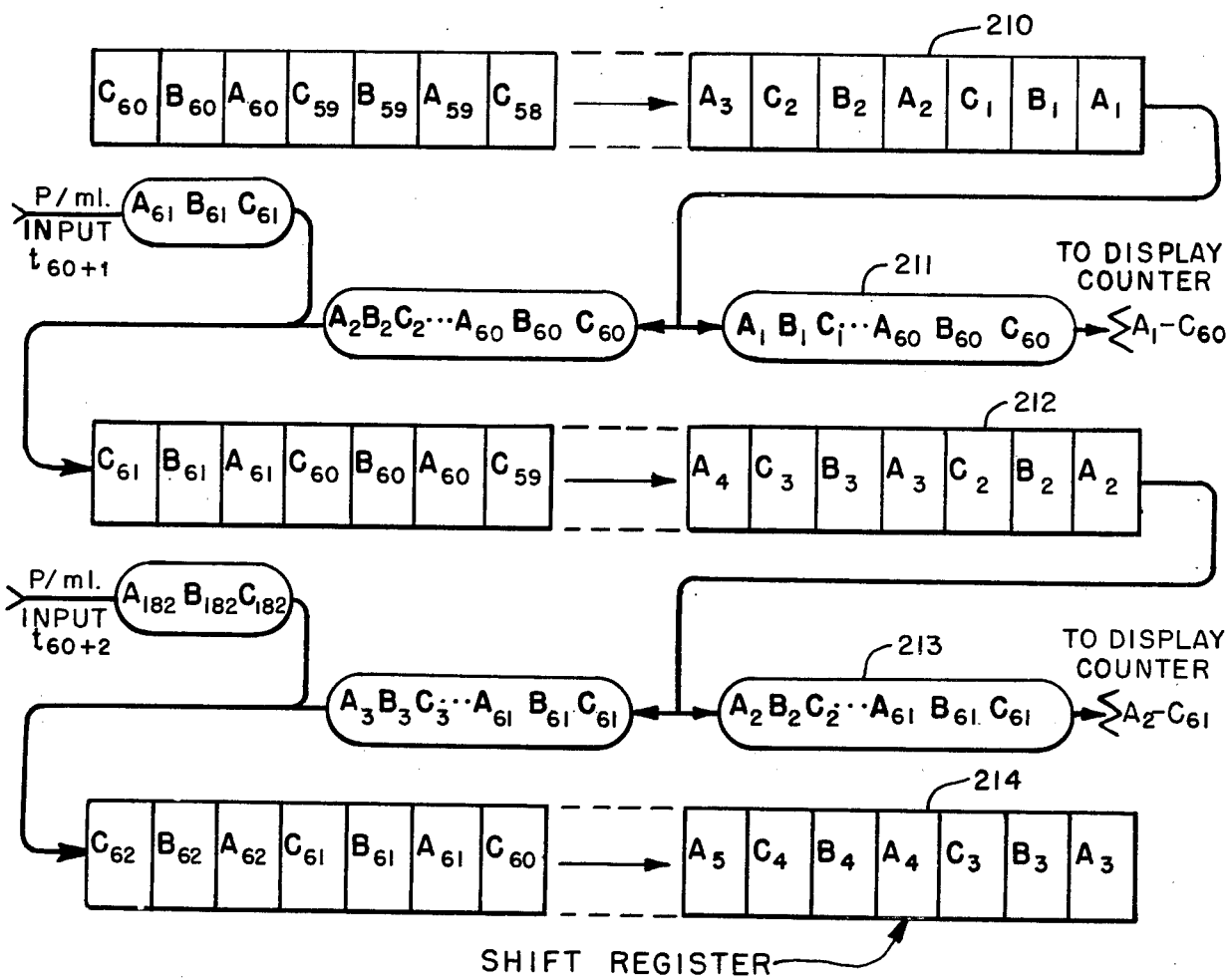
FIG. 13 is a depiction of hypothetical data flow useful in understanding the operation of the collection rate display system of FIG. 12.

Referring to FIG. 13, if each measurement interval is considered as having three data positions designated A, B and C, then after an initial 60 intervals shift register 200 may appear as shown by data group 210. If 180 clock pulses are now applied to the shift register an output data group 211 comprising data bits $A_1$ through $C_{160}$ will be applied to display counter 202. Subsequently, if new data $A_{61}$, $B_{61}$ and $C_{61}$ is introduced into the register, the $A_1$, $B_1$ and $C_1$ data is lost and the register contains data as shown by data block 212. This data is read to display counter as $A_2$–$C_{61}$ as shown by data block 213. If a third set of data comprising $A_{62}$–$C_{62}$ is entered, then the next oldest data $A_2$–$C_2$ is dropped, and the shift register assumes the data state shown by data block 214.

Figure 14:
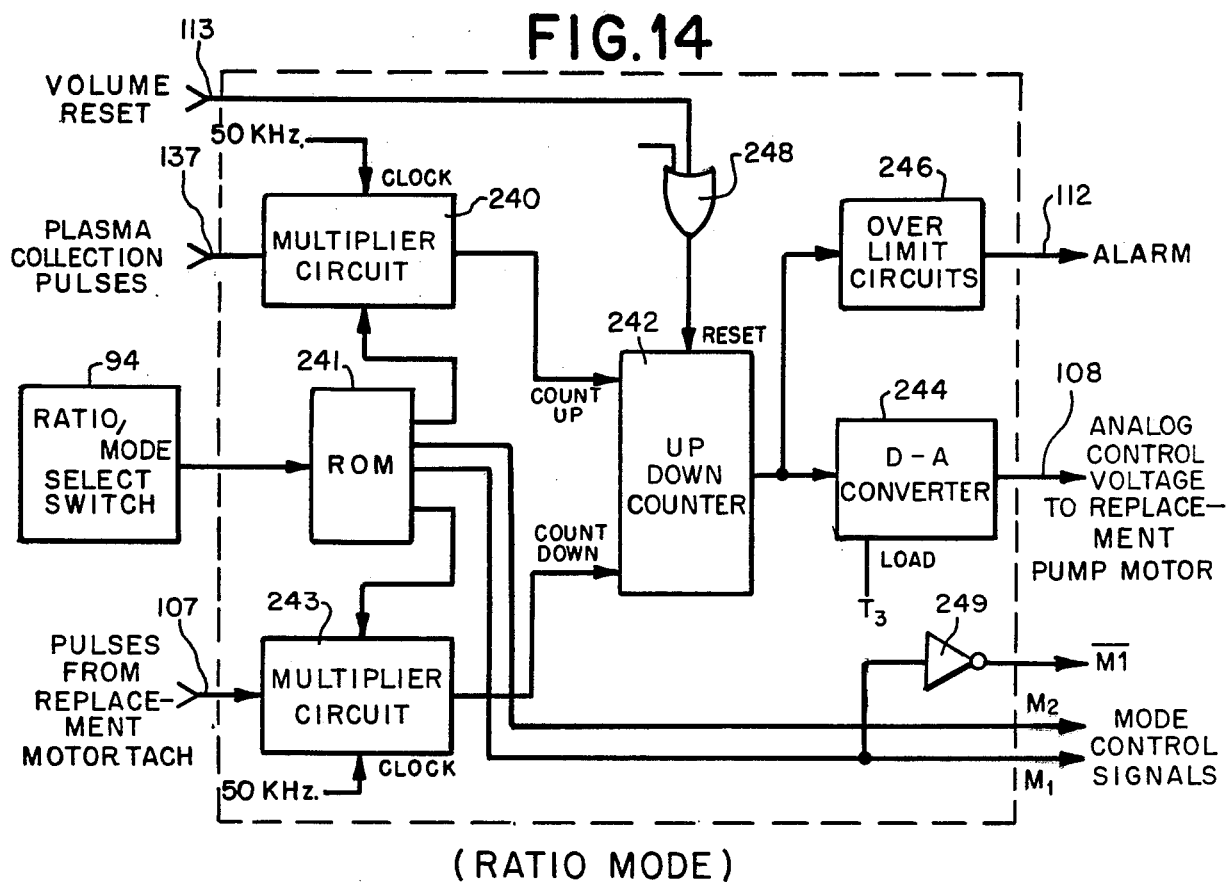
FIG. 14 is a simplified functional block diagram of the fluid reinfusion rate control system of the plasmapheresis system of FIGS. 1 and 2.

Referring to FIG. 14, the collection pulses developed by the volume derivation circuits 103 of the invention are also utilized by rate control circuits 106 to automatically control the rate at which collected plasma is replaced, and to provide an autologous mode wherein collected plasma can be treated and returned to the donor. Basically, this system, which is described in detail in the previously identified copending application of Arnold C. Bilstad and John T. Foley, entitled, "Blood Fractionation Apparatus Having Replacement Ratio Control System", includes a rate multiplier circuit 240 to which the 1 milliliter collection pulses developed by volume derivation circuits 103 are applied. Rate multiplier circuit 240 provides, in accordance with conventional practice, a selected number of pulses for each applied collection pulse. The number of pulses provided is dependent on an applied binary control signal developed within a read-only-memory (ROM) 241. The magnitude of the binary control signal, and hence the multiplication factor of the rate multiplier circuit 240, is dependent on an input signal applied to ROM 241 by the ratio/mode select switch 94. The output of rate multiplier circuit 240 is applied to the up count input of an up-down counter 242.

Within reinfusion rate control circuits 106 the tach output pulses from reinfuse motor tachometer 77 applied to a second rate multiplier circuit 243. The multiplication factor applied by this rate multiplier circuit is also dependent on an applied binary control signal developed by ROM 241, which is in turn also dependent on the ratio selected by the ratio/mode select switch 94. Thus, for a particular selected ratio, a predetermined number of output pulses will be produced by rate multiplier circuit 243 for each tach pulse received from tach 77. The output of rate multiplier circuit 243 is applied to the down count input of up-down counter 242.

With rate multiplier circuits 240 and 243 thus connected, the up-down counter 242 counts a predetermined number of counts in an up direction for each increment of plasma volume (weight) collected, and a predetermined number of counts in a down direction for each pulse received from the reinfuse pump motor tachometer. The counting state of the up-down counter 242 is indicated by a binary output signal. This signal is applied to a digital-to-analog converter 244 which converts the applied binary signal to an analog control voltage. This control voltage is applied by means of a control line 108 to the rate determining circuit 63 of reinfusion pump motor 76.

In operation, as plasma is collected in plasma collection container 42 transducer conversion circuits 102 produce output pulses at a frequency dependent on the weight of the collected plasma. Within volume derivation circuits 103 these weight-related transducer signals are converted to an output signal providing one pulse per milliliter of plasma collected. These plasma collection pulses are applied within reinfusion ratio control circuits 106 to rate multiplier circuit 240, which provides a predetermined number of pulses to up-down counter 242 for each applied collection pulse, depending on the multiplication factor set by ROM 241. This causes up-down counter 242 to count up to successively higher counting states. Digital to analog converter 244 responds by generating an analog control voltage which increases in level with the increasing count. This control voltage causes motor control circuit 78 to energize motor 76 so as to pump replacement fluid into the flow system.

As motor 76 turns tach 77 provides output pulses which are carried on tach line 107 to rate multiplier circuit 243. In multiplier circuit 243 a multiplication factor is introduced dependent on the applied control signal from ROM 241. The resulting rate-multiplied pulses are applied to the down count input of up-down 242. These pulses cause that counter to count down, thereby tending to reduce the analog control voltage developed by digital-to-analog converter 244. Thus, a closed loop system is formed which functions to maintain a continuous count of plasma collected less replacement fluid infused by tending to keep up-down counter 242 at a zero counting state.

By varying the multiplication factors of rate multiplier circuits 240 and 243 it is possible to maintain a predetermined volume ratio between plasma collected and replacement fluid added. In this regard, the factor applied by rate multiplier circuit 240 may be considered the numerator, and the factor applied by rate multiplier circuit 243 may be taken as the denominator of the ratio maintained by the system. The necessary multiplication factors are set by ROM 241 in response to volume ratio selected by switch 94. For example, if a 1:0 ratio is selected, both rate multiplier circuits are set for a multiplication factor of 4 and up-down counter 242 receives four pulses for each increment of plasma collected and four pulses for each increment of fluid replaced. If a ratio of 0.5 is set, then rate multiplier circuit 243 is set for a factor of 4, and rate multiplier circuit 240 is set for a factor of 2. If a ratio of 2.0 is to be maintained, then rate multiplier circuit 243 is set to a factor of 4, and rate multiplier circuit 240 is set for a factor of 8. In this way, a range of ratios from 0.5 to 3.5 is obtained in the illustrated plasmapheresis apparatus by the replacement rate control circuit 106.

To prevent operation of the plasmapheresis apparatus in the event that the reinfuse pump is unable to maintain the desired ratio, such as might occur were it to stall, the control circuit includes an overlimit circuit 246 which monitors the output of up-down counter 242 and provides an alarm output in the event the counter exceeds a predetermined maximum count. The alarm signal is conveyed over lead 112 through cable 27 for application to processor control circuit 81 to terminate operation of the plasmapheresis apparatus.

Since the operation of up-down counter 242 continues over continuous sampling periods, the counter is not reset following each measurement interval. Instead, the counter 242 is reset only upon a total volume reset, as when changing operating modes or upon initial power-up of the apparatus. Reset line 113 provides the necessary reset signal from the plasmapheresis apparatus through conductor 27.

An additional function of ROM 241 is to set the operating mode of the plasmapheresis monitor and control unit 22. To this end, ROM 241 provides M1 and M2 mode control signals according to the position of switch 94. These control signals are applied to the various circuits of the monitor and control unit to control and condition the circuits in accordance with the selected mode. When a reinfusion ratio is selected by switch 94, the M1 and M2 mode control signals are logic low to condition the circuits to the exchange mode. When the switch is positioned to the position both control signals are logic high to condition the autologous mode. An additional SCALE switch position, which allows weight-indicative transducer circuit pulses to be applied to rate readout 93, is provided by M1 being logic low and M2 being logic high. The operation of the apparatus in these modes is described in detail in the previously identified copending application of Arnold C. Bilstad and John T. Foley, entitled, "Blood Fractionation Apparatus Having Replacement Fluid Ratio Control Systems".

Figure 15:
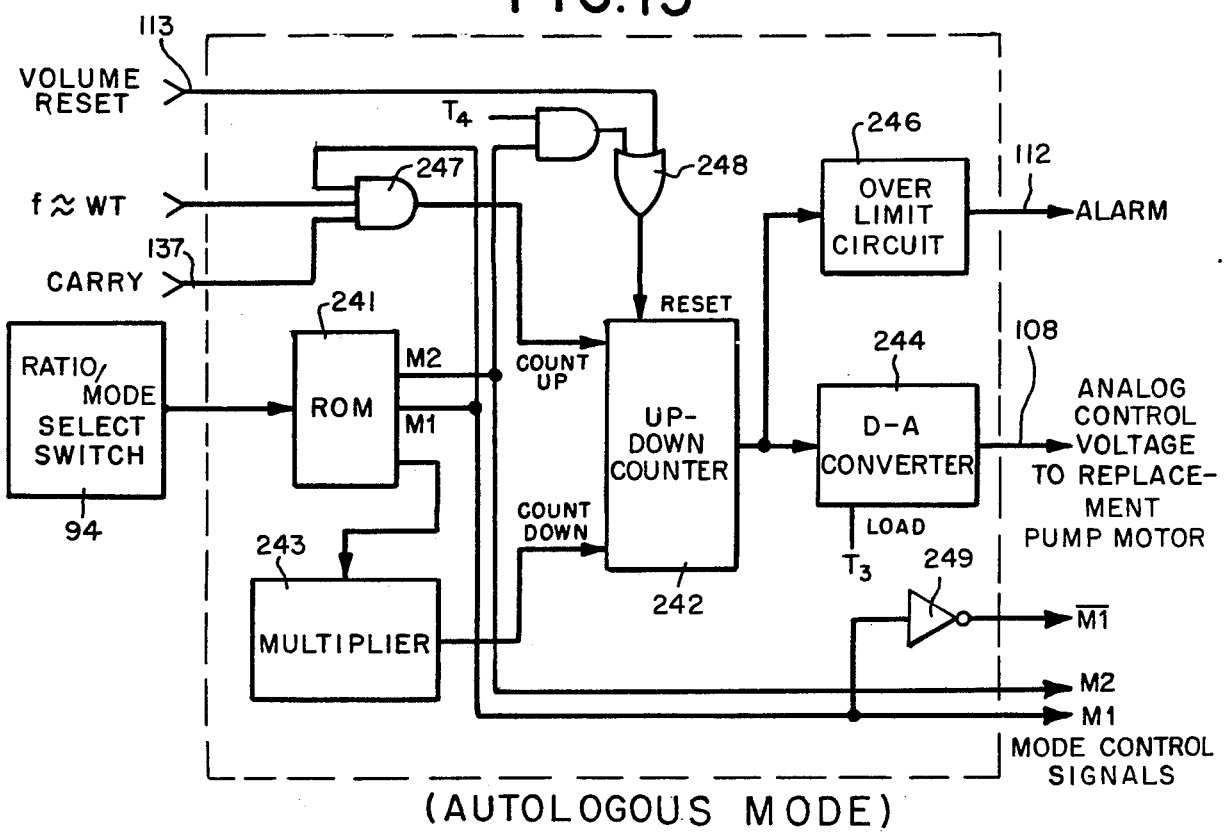
FIG. 15 is a simplified functional block diagram of the fluid reinfusion rate control system of FIG. 14 configured for autologous operation.

In the autologous mode of plasmapheresis apparatus 20 an alternative flow system (not shown) is provided wherein collected plasma is pumped from collection container 42 to a secondary processing system for treatment, and then returned to a secondary processing system for treatment, and then returned to bubble detector 44 for recombination with the processed blood and return to the donor. Referring to FIG. 15, when replacement ratio control circuits 106 are configured for operation in this mode the variable frequency pulses developed by transducer conversion circuits 102 are applied to the up-count input of up-down counter 242 through an AND gate 247. The remaining input of AND gate 247 is connected to carry line 137, so that when the carry line is positive, indicating a positive difference between present and stored collected plasma volume, the AND gate is enabled and counter 242 is caused to count up in response to the pulses. Rate multiplier circuit 243 is at this time conditioned by ROM 241 to a zero counting state; so that a continuous logic high output is applied by the multiplier circuit to the down count input of counter 242. This enables the counter to respond to the pulses applied to its up count input. No reinfusion pulses from volume derivation circuits 103 or tach pulses from replacement motor tachometer 77 are utilized in this operating mode.

An OR gate 248 allows the up-down counter 242 to be reset by either 1 hertz clock pulses or by a reset signal on the volume reset line 113. As in the ratio mode, over limit circuits 246 provide an alarm output in the event that the count in up-down counter 242 exceeds a predetermined limit, indicating that the balance in the plasma collection container 42 is not being maintained within limits.

Within volume derivation circuits 103 the M1 control signal developed by ROM 241 inhibits AND gates 136 and 139 (FIG. 6). This prevents the application of the $T_3$ (transfer) clock pulses to register 132 otherwise applied during each compute period. As a result, the register assumes and maintains the count of counter 130 at the time the apparatus is conditioned to the autologous mode. Counter 130 continues to receive and count pulses developed by transducer conversion circuits 102 during each measurement interval, and binary adder 131 develops the difference between each successive count of counter 130 and the stored count of register 132. However, the collection pulses developed by parallel-to-serial converter 134 are not applied to display counter 135 by reason of AND gate 136 being inhibited by the M1 mode control signal. Similarly, rate indicative pulses from shift register 200 are not applied to display counter 202 by reason of AND gate 201 being inhibited by the M1 mode control signal. Thus, in the autologous mode, readouts 62 and 64 are both rendered inoperative.

The application of transducer output pulses to the up-down counter is initiated upon the carry output of binary adder 131 becoming positive. This occurs when the count reached by input counter 130 exceeds the count stored by register 132. Upon the carry output becoming positive, AND gate 247 is enabled and all subsequent transducer pulses developed by frequency divider 126 are applied to up-down counter 242. This causes counter 242 to count up, resulting in the development of an analog control voltage by converter 244 upon occurence of the next occurring $T_3$ (latch) clock signal. The analog control voltage causes replacement motor 76 to operate to withdraw fluid from collection container 42. When sufficient fluid has been withdrawn from the collection container such that the count reached by counter 130 does not exceed the count stored in register 132, the carry output of binary adder 131 no longer becomes positive for any portion of the measurement interval and no transducer circuit output pulses are applied to up-down counter 242. Consequently, no analog control voltage is produced by converter 244 and the replacement motor 76 does not operate.

Thus, the volume derivation system of the invention provides a digital readout of collected volume which is not affected by disturbances to the system or by changing of the collection container. In performing a plasmapheresis procedure, it is only necessary to install and prime the flow system. No determination of tare weight is required, since the system recognizes only incremental changes of plasma volume.

The volume derivation system also provides an output signal which indicates increments of plasma collected. In the illustrated plasmapheresis apparatus this signal is in the form of collection pulses which are utilized by a rate display circuit and by a replacement fluid ratio control circuit. However, it will be appreciated that the signal can be provided in other forms, such as a multiple digit binary form, and utilized for other purposes, such as direct input to a system monitoring computer.

While the volume derivation system of the invention has been shown in conjunction with blood fractionation apparatus, it will be appreciated that the system finds application in other quantity measurement applications where a material is incrementally added to a container over a period of time.

Furthermore, while a deflected beam-type transducer has been shown with the collection container suspended below, other types of transducers and mounting arrangements may be utilized instead. For example, a transducer mechanically coupled to a pan on which the collection container is set may be provided on the top surface of the processor unit housing.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. In a collection apparatus for collecting a fluid in a collection container, wherein the fluid has a predetermined range of collection rates, a collection monitoring system comprises, in combination:

weight responsive means including an electrical transducer in supporting relationship to said container for providing an output signal indicative of the weight of the collection container and the collected fluid container therein;

comparison means for repetitively comparing successive output signals to develop difference signals indicative of changes in weight of the collection container over successive measurement intervals; and incrementing means responsive only to difference signals representing collection rates within the range of collection rates for producing collection signals indicative of incremental units of fluid volume added to the collection container.

2. A fluid collection apparatus as defined in claim 1 including volume indicator means responsive to said collection signals for providing an output indicative of the cumulative count of said incremental units, and hence the volume of fluid collected in the collection container.

3. A fluid collection monitoring system as defined in claim 2 wherein said volume indicator means comprise a counter for accumulating the sum of said collection signals.

4. A fluid collection monitoring system as defined in claim 3 wherein said counter comprises a latch register and said volume indicator means include a digital display device connected to the output of said register.

5. A fluid collection monitoring system as defined in claim 1 wherein said incrementing means is inhibited for a predetermined period of time following said difference signal exceeding the range of collection rates.

6. A fluid collection monitoring system as defined in claim 1 wherein said comparison means compare a present output signal with the most immediate preceding output signal which provided a difference signal within the range of collection rates.

7. A fluid collection monitoring system as defined in claim 6 wherein said comparison means compare a present output signal with the most immediate preceding output signal which provided a difference signal within the range of collection rates.

8. In an apparatus for collecting a fluid in a collection container, and having a predetermined range of collection rates, a collected volume display system comprising, in combination:

weight responsive means including an electrical transducer in supporting relationship to the collection container providing an output signal indicative of the weight of the collection container and the collected fluid contained therein;

comparison means for repetitively comparing said transducer output signal over a predetermined measurement interval with said output signal over a preceding measurement interval to develop difference signals indicative of changes in weight over successive measurement intervals;

incrementing means responsive only to difference signals which correspond to collection rates within said predetermined range, for producing collection signals indicative of incremental units of fluid volume added to the collection container; and volume indicator means responsive to said collection signals for providing an output indicative of the cumulative count of said incremental units, and hence the volume of the fluid collected in the collection container.

9. A fluid collection monitoring system as defined in claim 8 wherein said comparison means include a binary adder, and said volume indicator means include a display counter for receiving data from said output circuit means.

10. A fluid collection monitoring system as defined in claim 9 wherein said incrementing means include parallel-to-serial signal conversion means for generating serial pulses indicative of the output of said binary adder, and wherein said pulses are applied to and counted by said display counter.

11. In a fluid collection apparatus for collecting a fluid in a collection container, and of the type having a predetermined range of collection rates and utilizing a disposable flow system having a collection container for the collected component, a collected volume display system comprising, in combination:

weight responsive means including an electrical transducer providing an output signal having a frequency related to the weight of the collection container and the collected fluid container therein;

comparison means for repetitively comparing the frequency of said transducer output signal over a present measurement interval with the frequency of said output signal over a preceding like measurement interval to periodically develop difference signals indicative of any change in units of volume collected during the measurement interval;

volume indicator means including a display counter responsive to applied collection signals for providing an output indicative of the sum of said incremental units; and incrementing means for applying only difference signals indicating the collection of fluid increments within said range of collection rates as collection signals to said counter whereby said indicator means indicate the volume of fluid collected in the collection container notwithstanding physical disturbances to the container.

12. A fluid collection monitoring system as defined in claim 11 wherein said incrementing means is inhibited for a predetermined period of time following said difference signal exceeding the maximum collection rate.

13. A fluid collection monitoring system as defined in claim 11 wherein said comparison means include a binary adder, and said volume indicator means include a display counter for receiving data from said incrementing means.

14. A fluid collection monitoring system as defined in claim 13 wherein said incrementing means include parallel-to-serial signal conversion means for generating serial collection pulses indicative of the output of said binary adder, and wherein said pulses are applied to and counted by said display counter.

15. A fluid collection monitoring system as defined in claim 11 wherein said measurement intervals comprise one second.

16. In a fluid collection apparatus for collecting a fluid, and of the type having a predetermined range of collection rates and a disposable flow system having a collection container for the collected fluid, a collected volume display system comprising, in combination:
weight responsive means including an electrical transducer supporting the collection container for providing an output signal having a frequency indicative of the weight of the collection chamber and the collected fluid contained therein;
input counter means responsive to said weight-indicative signal for providing an output signal representative of the frequency of said collection pulses;
means for periodically applying said weight-indicative signal to said input counter for a predetermined measurement interval to develop said output signal therein;
storage means for storing said output signal subsequent to said measurement interval;
comparison means for comparing said output signal with said stored output signal in said storage means to develop a difference signal indicative of incremental volume units of fluid collected during the measurement interval;
volume indicator means including a counter responsive to applied collection signals for providing an output indicative of the cumulative count of said applied collection signals; and
incrementing means for applying only said difference signals which correspond to a collection rate within the range of collection rates to said counter whereby said volume indicator means display collected volume notwithstanding external disturbances to the collection container.

17. A fluid collection monitoring system as defined in claim 16 wherein said comparison means include a binary adder, and said volume indicator means include a display counter for receiving data from said incrementing means.

18. A fluid collection monitoring system as defined in claim 17 wherein said incrementing means include parallel-to-serial signal conversion means for generating serial pulses indicative of the output of said binary adder, and wherein said pulses are applied to and counted by said display counter.

19. A blood fractionation monitoring system as defined in claim 16 including means for enabling said storage means to assume the output count of said input counter only when said difference is within the range of collection rate.

20. A blood fractionation monitoring system as defined in claim 19 wherein said storage means comprise a latch register.

21. A fluid collection monitoring system as defined in claim 16 wherein said incrementing means is inhibited for a predetermined period of time following said difference signal exceeding the range of collection rates.

22. A fluid collection monitoring system as defined in claim 16 including means for enabling said storage means to assume the output count of said input counter only when said difference is less than the range of system collection rates.

23. In a blood fractionation apparatus for separating and collecting a blood fraction from whole blood, wherein the blood fraction has a predetermined range of collection rates, and of the type utilizing a disposable flow system having a collection container for the collected component, a blood component collection monitoring system comprising, in combination:
weight responsive means including an electrical transducer in supporting relationship to the collection container for providing an output signal indicative of the weight of the collection container and the collected blood fraction contained therein;
comparison means for repetitively comparing successive output signals to develop difference signals indicative of the changes in weight of the collection container over successive measurement intervals; and
incrementing means responsive only to difference signals representing collection rates within the predetermined range of collection rates for producing collection signals indicative of incremental volume units of blood component added to the collection container.

24. A blood fractionation monitoring system as defined in claim 23 including volume indicator means responsive to said collection signals for providing an output indicative of the sum of said incremental units, and hence the volume of the blood fraction collected.

25. A blood fractionation monitoring system as defined in claim 23 wherein said volume indicator means comprise a counter for accumulating said collection signals.

26. A blood fractionation apparatus as defined in claim 23 wherein said incrementing means is inhibited for a predetermined period of time following said difference exceeding the range of collection rates.

27. In an apparatus for separating and collecting a blood fraction from whole blood, and of the type having a predetermined range of collection rates and utilizing a disposable flow system having a collection container for the collected component, a collected volume display system comprising, in combination:
weight responsive means including an electrical transducer in supporting relationship to the collection container and providing an output signal indicative of the weight of the collection chamber and the collected blood fraction container therein;
comparison means for repetitively comparing said transducer output signal over a predetermined measurement interval with said output signal over a preceding measurement interval to develop difference signals;
incrementing means responsive only to difference signals which correspond to collection rates within said predetermined range of collection rates for producing collection signals indicative of incremental volume units of blood fraction added to the collection container; and
volume indicator means responsive to said collection signals for providing an output indicative of the sum of said incremental units, and hence the volume of the blood fraction collected in the collection container.

28. A blood fractionation monitoring system as defined in claim 27 wherein said comparison means include a binary adder, and said volume indicator means include a display counter for receiving data from said incrementing means.

29. A blood fractionation monitoring system as defined in claim 28 wherein said incrementing means include parallel-to-serial signal conversion means for generating serial pulses indicative of the output of said binary adder, and wherein said pulses are applied to and counted by said display counter.

30. A blood fractionation apparatus as defined in claim 27 wherein said incrementing means is inhibited for a predetermined period of time following said difference exceeding the range of collection rates.

31. In a blood fractionation apparatus for separating and collecting a blood fraction from whole blood, and of the type having a predetermined range of collection rates and utilizing a disposable flow system having a collection container for the collect component, a collected volume display system comprising, in combination:

weight responsive means including an electrical transducer providing an output signal having a frequency related to the weight of the collection chamber and the collected blood fraction contained therein;

comparison means for repetitively comparing the frequency of said transducer output signal over a present measurement interval with the frequency of said output signal over a preceding measurement interval to develop difference signals;

volume indicator means including a display counter responsive to applied difference signals; and incrementing means for applying only difference signals indicating the collection of blood fraction increments within said range of collection rates to said display counter whereby said indicator means indicate the volume of the blood fraction collected in the collection container notwithstanding physical disturbances to the container.

32. A blood fractionation monitoring system as defined in claim 31 wherein said incrementing means is inhibited for a predetermined period of time following said difference exceeding said range of collection rates.

33. A blood fractionation monitoring system as defined in claim 31 wherein said incrementing means include parallel-to-serial signal conversion means for generating serial pulses indicative of the output of said binary adder, and wherein said pulses are applied to and counted by said display counter.

34. A blood fractionation monitoring system as defined in claim 31 wherein said measurement intervals comprise one second.

35. In a blood fractionation apparatus for separating and collecting a blood fraction from whole blood, and of the type having a predetermined range of collection rates and utilizing a disposable flow system having a collection container for the collected component, a collected volume display system comprising, in combination:

weight responsive means including an electrical transducer in supporting relationship to the collection container for providing an output signal having a frequency indicative of the weight of the collection container and the collected blood fraction contained therein;

input counter means responsive to said weight indicative signal for providing a first output signal representative of the frequency of said weight signal;

means for periodically applying said weight indicative signal to said input counter for a predetermined measurement interval to develop said output signal therein;

storage means for storing said output signal subsequent to said measurement interval;

comparison means for comparing said output signal with the stored signal in said storage means to develop a difference signal indicative of incremental volume units of the fraction collected during the measurement interval; and volume indicator means including a counter responsive to applied collection signals for providing an output indicative of the cumulative count of said collection signals; and incrementing means for applying only said difference signals which correspond to a collection rate within the range of collection rates as collection signals to said counter whereby said volume indicator means display collected volume notwithstanding external disturbances to the collection container.

36. A blood fractionation monitoring system as defined in claim 35 wherein said comparison means include a binary adder, and said volume indicator means include a display counter for receiving data from said incrementing means.

37. A blood fractionation monitoring system as defined in claim 36 wherein said incrementing means include parallel-to-serial signal conversion means for generating serial pulses indicative of the output of said binary adder, and wherein said pulses are applied to and counted by said display counter.

38. A blood fractionation monitoring system as defined in claim 35 including means for enabling said storage means to assume the output count of said input counter only when said difference is less than the range of system collection rates.

39. A blood fractionation monitoring system as defined in claim 38 wherein said storage means comprise a latch register.

40. A blood fractionation apparatus as defined in claim 35 wherein said incrementing means is inhibited for a predetermined period of time following said difference exceeding the range of collection rates.

41. In a blood fractionation apparatus for separating and collecting a blood fraction from whole blood, and having a predetermined range of collection rates, and of the type utilizing a disposable flow system having a collection container for the collected component, a collected volume display system comprising, in combination:

suspension means for said collection container including an electrical transducer providing an output signal having a voltage level indicative of the weight of the collection chamber and the blood fraction container therein;

conversion circuit means responsive to said transducer output signal for generating output pulses having a frequency dependent on said voltage level;

an input counter;

means for periodically applying said output pulses to said input counter for predetermined measurement intervals to develop output signals corresponding to the frequency of said pulses within each said measurement interval;

means including a latch-type register for storing the output signal developed dureing each preceding measurement interval;

binary adder means for providing a difference signal following each measurement interval indicative of the difference between the output of said input counter and the output of said register;

incrementing means responsive to said difference signal for providing a related number of collection pulses only when said output is positive and within said range of collection rates; and a latch-type display counter for accumulating said collection pulses to provide an output indicative of the total volume of blood fraction collected.

42. A blood fractionation monitoring system as defined in claim 41 including latch control means for applying a latch signal to said latch register to enable said register only when said output of said input counter does not exceed the absolute of said predetermined range of collection rates.

43. In a collection apparatus for collecting a fluid in a collection container, the fluid having a predetermined range of collection rates, the method of monitoring collected fluid volume comprising:

supporting the collection container on an electrical transducer to obtain an output signal related to the weight of the container and the collected fluid contained therein;

comparing the output signal over a present measurement interval with the output signal over a previous measurement interval to develop difference signals indicative of the collection of incremental units of volume, and excluding those difference signals which are negative or which exceed a predetermined maximum rate to develop collection signals indicative of incremental volumes of fluid collected.

44. The method of monitoring collected volume as defined in claim 43 including summing the collection signals to develop an output indicative of the total volume of fluid collected in the collection container.

45. The method of monitoring collected volume as defined in claim 43 including inhibiting the comparison for a predetermined period of time following a collection signal exceeding the predetermined maximum collection rate.

46. The method of monitoring collected volume as defined in claim 45 including comparing the output signal in the previous measurement interval with the output signal in a subsequent measurement interval following a difference signal exceeding the predetermined range of collection rates.

* * * * *